US010213621B2

(12) United States Patent
Bush et al.

(10) Patent No.: US 10,213,621 B2
(45) Date of Patent: Feb. 26, 2019

(54) TRAJECTORY OPTIMIZATION IN RADIOTHERAPY USING SECTIONING

(71) Applicant: The Board of Trustees of the Leland Stanford Junior University, Palo Alto, CA (US)

(72) Inventors: Karl Bush, Palo Alto, CA (US); Michael Hadsell, East Palo Alto, CA (US); Christopher Locke, Menlo Park, CA (US); Lei Xing, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 44 days.

(21) Appl. No.: 15/621,962

(22) Filed: Jun. 13, 2017

(65) Prior Publication Data

US 2017/0354832 A1 Dec. 14, 2017

Related U.S. Application Data

(60) Provisional application No. 62/422,731, filed on Nov. 16, 2016, provisional application No. 62/349,420, filed on Jun. 13, 2016.

(51) Int. Cl.
*A61N 5/10* (2006.01)
(52) U.S. Cl.
CPC ........... *A61N 5/103* (2013.01); *A61N 5/1047* (2013.01); *A61N 5/1081* (2013.01)
(58) Field of Classification Search
CPC .... A61N 5/103; A61N 5/1031; A61N 5/1047; A61N 5/1081; G06F 19/00; G06F 19/3481
See application file for complete search history.

(56) References Cited

U.S. PATENT DOCUMENTS 6,504,899 B2 * 1/2003 Pugachev ............... A61N 5/103
378/65
7,027,557 B2 * 4/2006 Llacer .................. A61N 5/1031
378/65

(Continued)

OTHER PUBLICATIONS

Wang, C., Luan, S., Tang, G., Chen, D. Z., Earl, M. A., & Cedric, X. Y. (2008). Arc-modulated radiation therapy (AMRT): a single-arc form of intensity-modulated arc therapy. Physics in Medicine & Biology, 53(22), 6291.*

*Primary Examiner* — Wyatt A Stoffa
(74) *Attorney, Agent, or Firm* — Lumen Patent Firm

(57) ABSTRACT

A radiation therapy treatment method includes providing a patient model, dosimetric constraints, delivery motion constraints, and delivery coordinate space of a radiation delivery device, where the delivery coordinate space is represented as a mesh with vertices connected by edges, where the vertices correspond to directions of a beam eye view (BEV) of the radiation delivery device, where each BEV has corresponding area elements resulting from beam collimation. BEV region connectivity manifolds are constructed from the patient model, the dosimetric constraints, the delivery coordinate space, and existing beam trajectories, wherein each of the BEV region connectivity manifolds represents connections between contiguous 2D target regions, where each of the 2D target regions is defined at each of the vertices of the delivery coordinate space. Beam trajectories are selected based on region connectedness information in the BEV region connectivity manifolds, the dosimetric constraints, the delivery motion constraints, and the existing beam trajectories. Radiation is delivered using the radiation delivery device in accordance with the beam trajectories.

8 Claims, 23 Drawing Sheets

(56) References Cited

U.S. PATENT DOCUMENTS

| | | | |
|---|---|---|---|
| 8,262,554 B2* | 9/2012 | Sayeh | A61B 6/032 378/65 |
| 9,050,459 B2* | 6/2015 | Otto | A61N 5/103 |
| 2002/0051513 A1* | 5/2002 | Pugachev | A61N 5/103 378/65 |
| 2005/0254622 A1* | 11/2005 | Llacer | A61N 5/1031 378/65 |
| 2013/0142310 A1* | 6/2013 | Fahimian | A61N 5/103 378/65 |
| 2017/0189717 A1* | 7/2017 | MacDonald | A61B 6/032 |

* cited by examiner

Fig. 2A (Prior Art)    Fig. 2B (Prior Art)
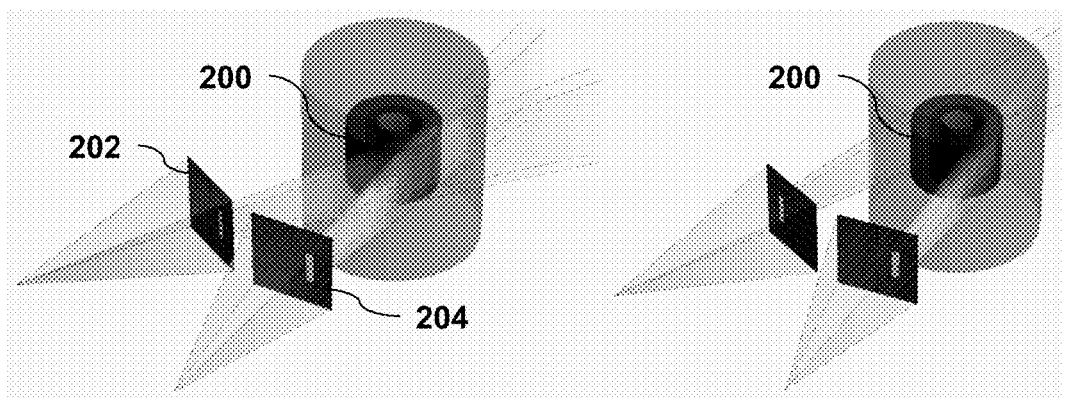
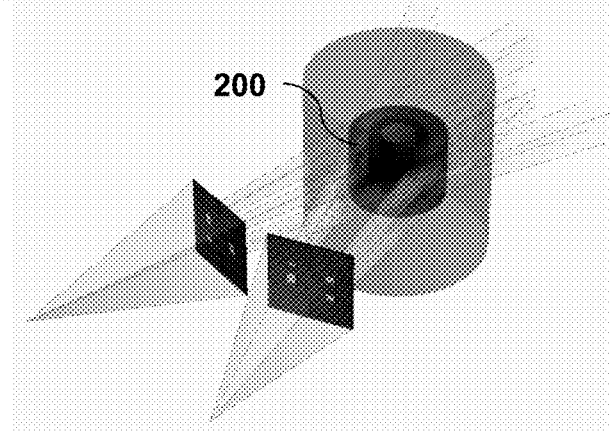
Fig. 2C (Prior Art)

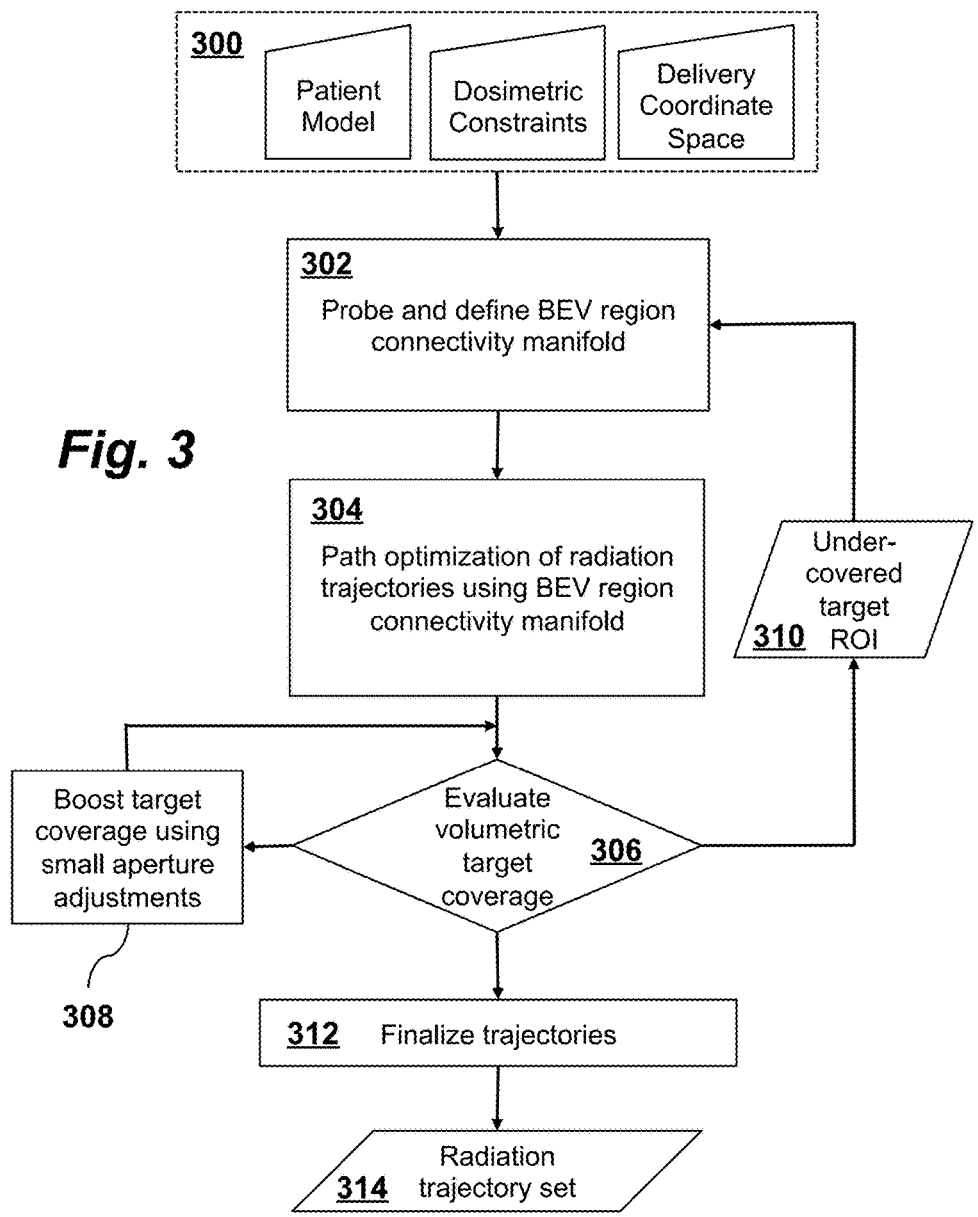

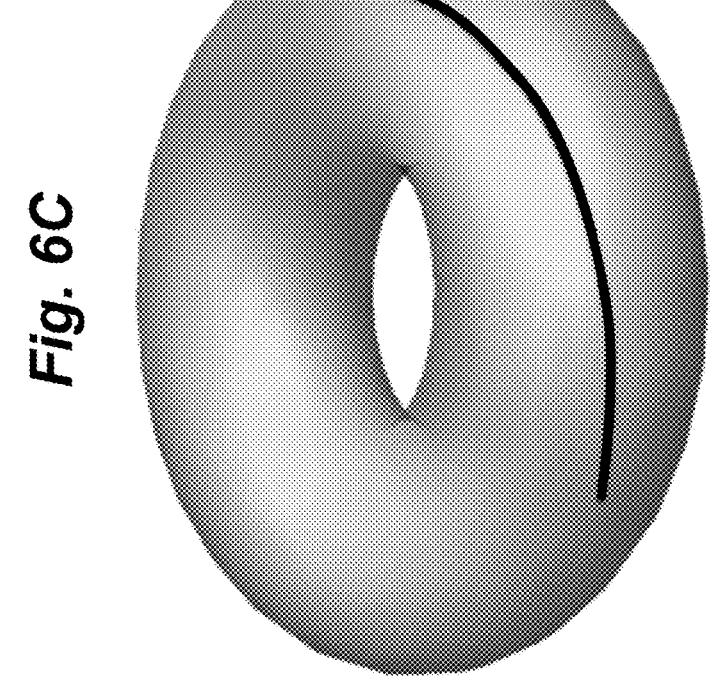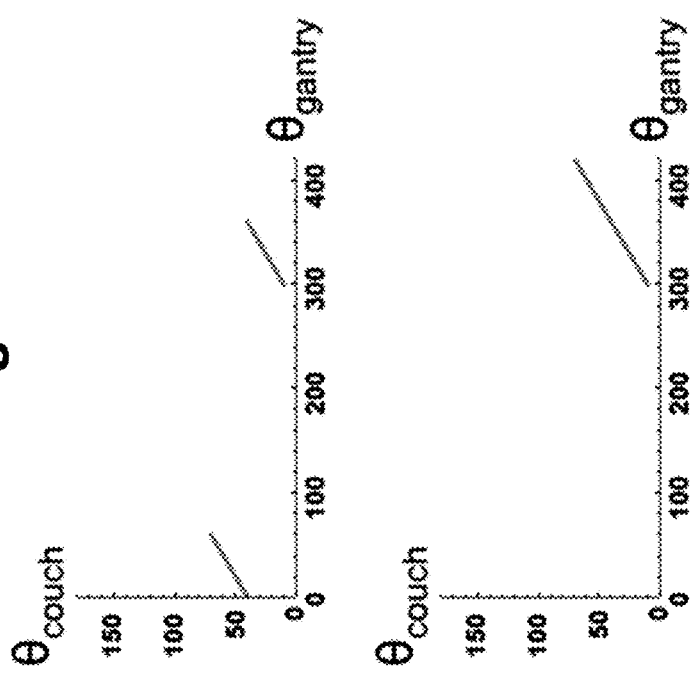

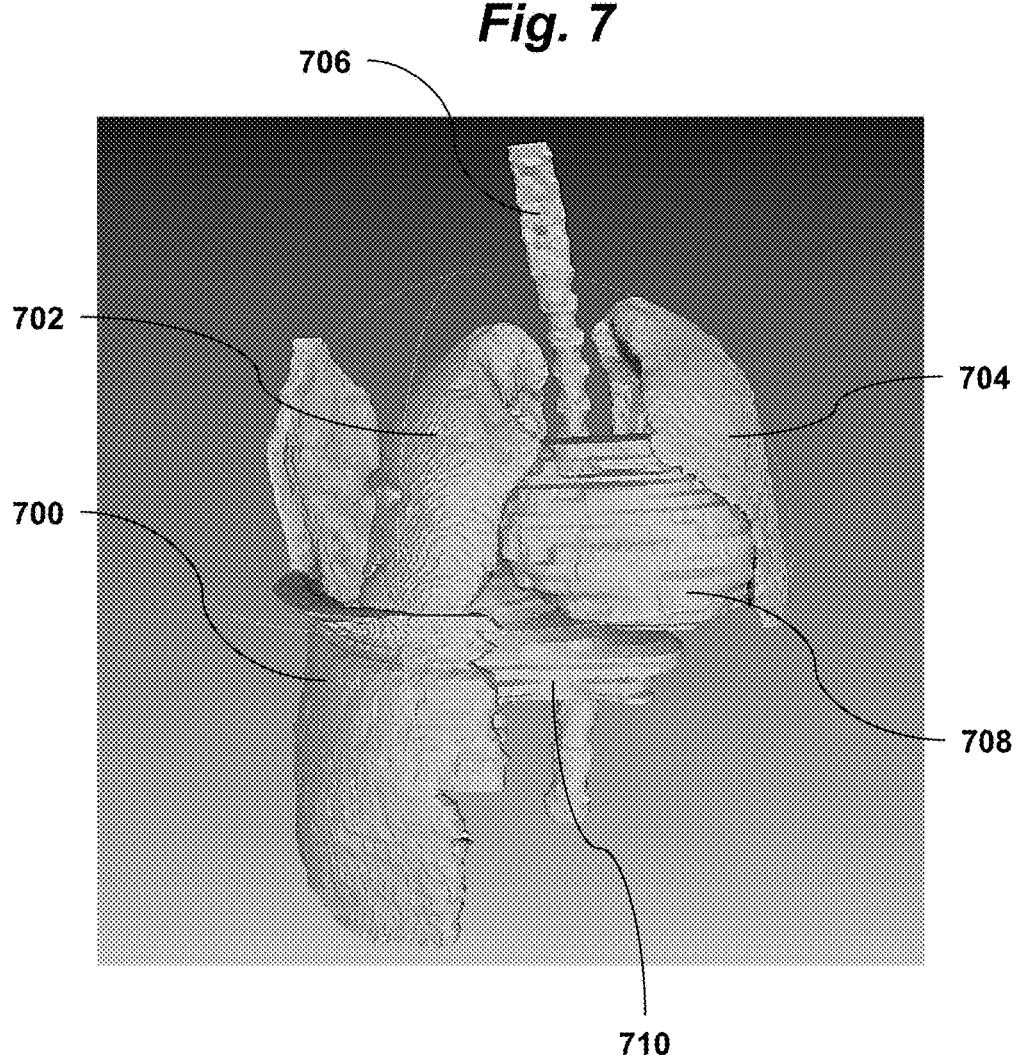

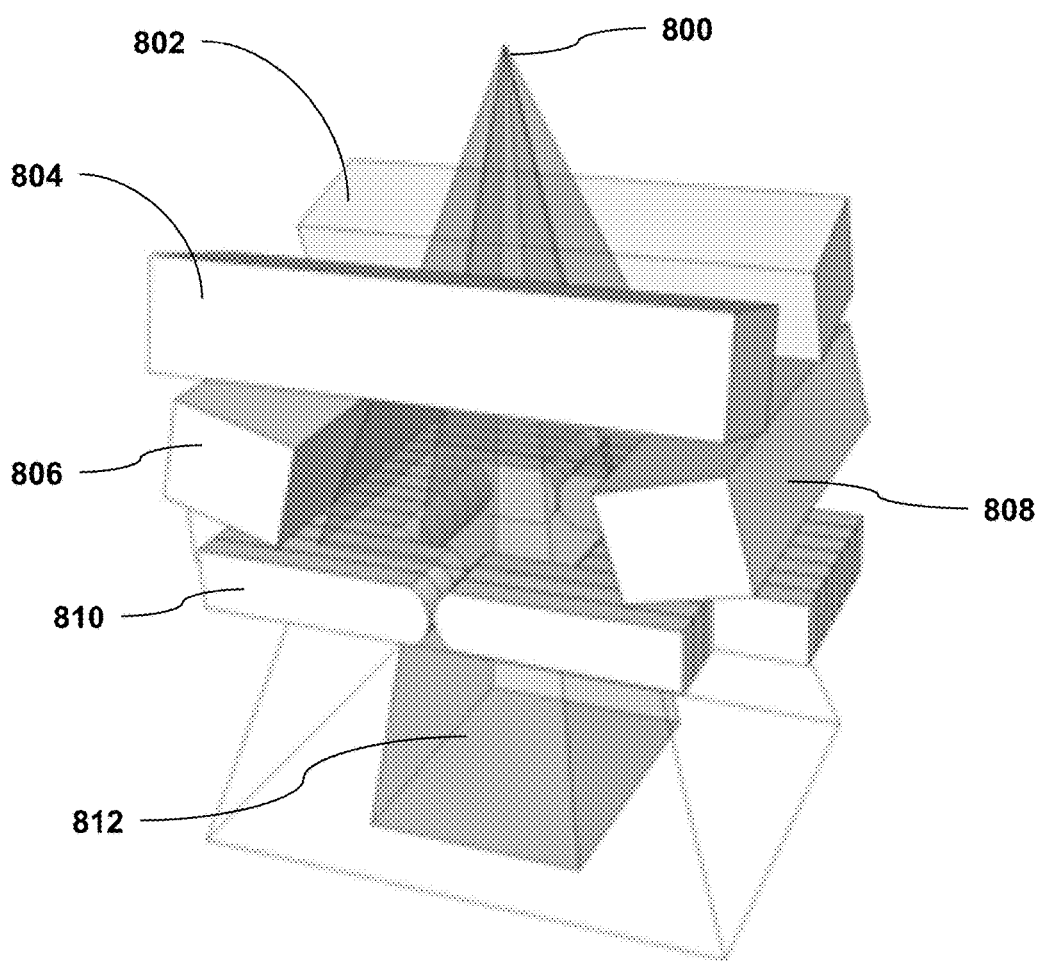

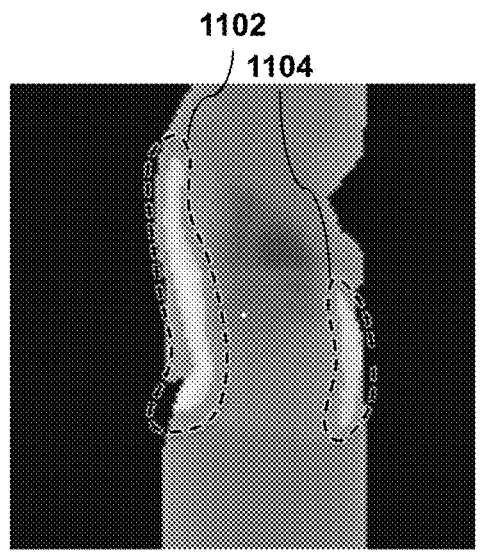
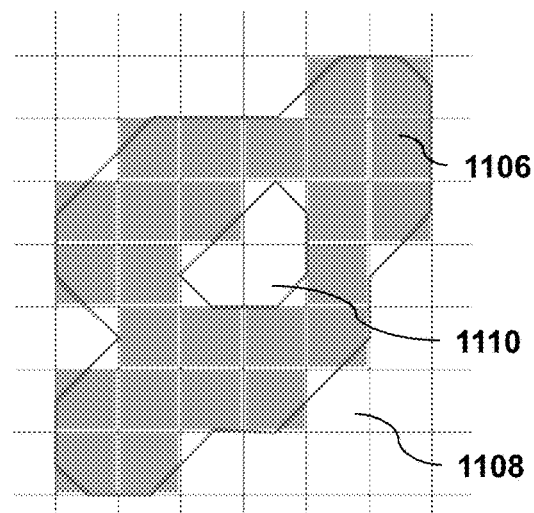
*Fig. 11A*  *Fig. 11B*
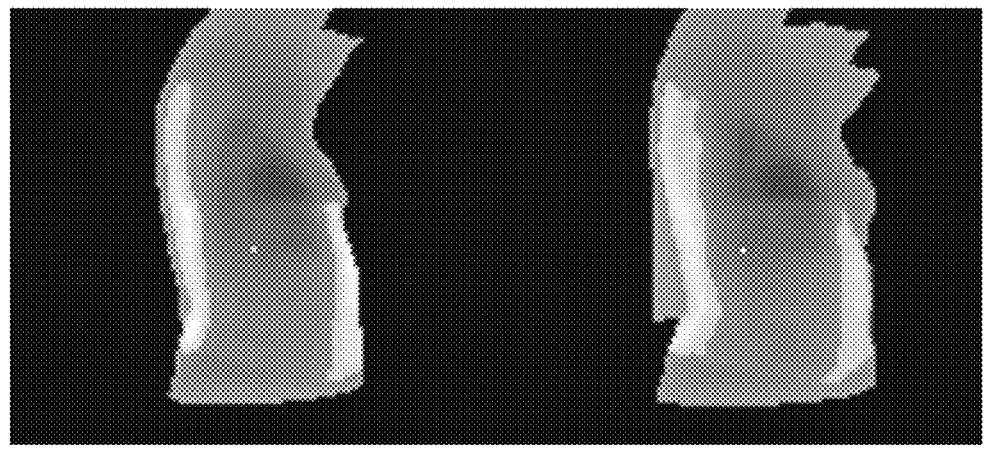
*Fig. 11C*  *Fig. 11D*

TRAJECTORY OPTIMIZATION IN RADIOTHERAPY USING SECTIONING

CROSS-REFERENCE TO RELATED APPLICATIONS

This application claims priority from U.S. Provisional Patent Application 62/349,420 filed Jun. 13, 2016, which is incorporated herein by reference. This application claims priority from U.S. Provisional Patent Application 62/422,731 filed Nov. 16, 2016, which is incorporated herein by reference.

STATEMENT REGARDING FEDERALLY SPONSORED RESEARCH OR DEVELOPMENT

None.

FIELD OF THE INVENTION

The present invention relates generally to radiotherapy and radiation treatment planning. More specifically, it relates to improved techniques for determining radiation beam trajectories.

BACKGROUND OF THE INVENTION

In recent years, radiotherapy has experienced a profound reduction in delivery times and improvement in plan quality with the establishment of dynamic gantry treatments such as Volumetric Modulated Arc Therapy (VMAT) [Otto, 2008, Yu, 1995]. The success of VMAT has no doubt motivated a substantial wave of research in furthering dynamic delivery capabilities of medical accelerator in routine treatment.

A natural progression beyond VMAT has led to increasing modulation capabilities and improved dose gradient formation through inclusion of dynamic collimator angle optimization such as in the work by Zhang et al. (2010), and in the work by Yang et al. (2011) who investigated the possibility of incorporating dynamic couch angle optimization to form a set of optimized arc trajectories. The concept of combining gantry rotation with a rotation of the patient couch was in fact first proposed by Podgorsak et al. (1988) for stereotactic brain treatment, to deliver a continuous single gantry arc with dynamic couch rotation so as to avoid producing opposed beam pairs. Complex for the time, the technique was not widely adopted into mainstream clinical use, possibly due to the risk associated with accurately administering a highly dynamic treatment without sufficient safety and verification technologies.

To define optimal couch-gantry angles, Pugachev and Xing (2001) developed the concept of Beam's Eye View Dose (BEVd), from which a score can be calculated from each BEV by evaluating normal tissue dose relative to well accepted tissue tolerances [Marks, 2010]. The approach was used in Intensity Modulated Radiation Therapy (IMRT) for beam angle optimization and later was implemented as a couch-gantry angle scoring method in arc therapy [Ma et al., 2009], Trajectory Modulated Arc Therapy (TMAT) optimization by Fahimian et al. (2013) and recently implemented in the Station Parameter Optimization in Radiotherapy (SPORT) algorithm by Kim et al. (2015).

Investigating the potential benefits of using radiation beams incident from all possible directions, Dong et al. (2013a, 2013b), performed a series of treatment plan optimizations starting with 1162 static beams with 6 degree separation spanning 4π solid angle. Dong et al. demonstrated substantially improved plan quality over coplanar VMAT plans using a method to select and optimize fluence from a high scoring subset of 14-22 of the 1162 static fields.

Smyth et al. (2013) developed another dynamic couch VMAT optimization method in which graph optimization is used to optimally traverse the deliverable gantry-couch space with graph nodes representing cost from the incident angle. The results demonstrated a modest improvement over coplanar VMAT for several treatment sites.

In 2015, 3 separate research groups made efforts toward trajectory optimization. MacDonald and Thomas (2015) implemented a geometrical BEV analysis to score incident angles using QUANTEC dose limits [Marks, 2010] and subsequently determined optimal trajectories based on a score map. Papp et al. (2015) developed a non-coplanar VMAT approach in which they first determine a set of high-scoring incident beams using a beam angle optimization and then connect the incident angles using a travelling salesman minimization approach. Wild et al. (2015) also implemented an approach of identifying high scoring incident angles and connecting the angles with a travelling salesman approach. Wild et al. also compared the dosimetric capabilities of many forms of coplanar and non-coplanar trajectory possibilities to a 4π static field IMRT plan consisting of 1374 incident IMRT beams. The set of 4π static field IMRT plans were found to produce a best overall baseline for a dosimetric comparison of the trajectory techniques and the travelling salesman approach was found to be a good choice when considering treatment delivery times.

It can be shown that all of the published trajectory optimization algorithms developed to date share the following common core approach, illustrated in FIGS. 1A-B: First, an incident beam angle scoring function is defined and used to map out the "goodness" of incident beam angles. The gantry-couch angle score map 100 in the figures show the score assigned to each gantry-couch angle pair, where lighter shading indicates higher score and darker shading indicates lower score; Second, collision zones 102, 104 are marked out for avoidance and then an optimization is performed to determine optimal trajectories 106 from the gantry-couch angle score map by linking or traversing the "goodness" map, avoiding the collision zones for the delivery device. Squares 108 and 110 in FIG. 1B represent the beam's eye view from points A and B on trajectory T. Oval 112 is a single region to treat at point A, and ovals 114 and 116 are two disconnected regions to treat at point B.

Using this common approach, a fundamental loss of information occurs: The connectedness of ideal regions to treat, from one incident angle to the next, is entirely lost. By using only a single calculated score for each incident beam angle, the geometrical relationship of adjacent apertures is not preserved and the deliverable trajectories ultimately degrade from inadequate dynamic multi-leaf collimator (MLC) delivery capabilities and MLC aperture forming contention issues. Consequently, the resulting trajectories cannot be considered optimal using any of the approaches summarized above.

A consequence of not considering the geometrical relationship of apertures forming a trajectory is further illustrated by considering the progressive resolution VMAT optimization example of a hollow cylindrical target 200 surrounding an organ at risk, as shown in FIGS. 2A-C. By cylindrical symmetry, all axial, coplanar incident beam angles can be shown to score equal "goodness". This target/avoidance geometry was constructed specifically to present 2 geometrically separate choices for each MLC leaf pair from every angle (MLC aperture contention).

To maximally shield the central organ at risk and treat the target, human intuition would find it logical to arrange a set of MLC leaf pairs 202, 204 to expose only one side 206 of the hollow cylinder and not traverse across the central avoidance for the entire duration of the trajectory such as in FIG. 2A. Yet, in this example, such a solution is probabilistically undiscoverable without some mathematical consideration of MLC synchronization. In FIG. 2B, a "confused" trajectory is illustrated with the confusion stemming from a lack of MLC aperture synchronization between the earliest/coarsest sampling stages of VMAT. In FIG. 2C, a second "confused" MLC is illustrated with the confusion stemming from a lack of MLC synchronization amongst the MLC leaf pairs of a given aperture. It is important to note that the aperture score is identical in each case.

SUMMARY OF THE INVENTION

In this work, we present a new perspective on trajectory optimization in radiotherapy using the concept of sectioning. The TORUS approach solves one of the most difficult problems in trajectory optimization, synchronization of the medical accelerator's dynamic delivery. TORUS avoids degradation of trajectory optimization quality by mapping the connectedness of target regions from the BEV, throughout the delivery coordinate space. This connectedness is then used in trajectory formation, rather than simply the incident angle score as current methods have implemented. We will show that by respecting the connectedness of target regions, optimal trajectories with fewer MLC contention issues are produced. Path optimization with a modified Dijkstra approach in TORUS produces dosimetrically optimal trajectories with highly efficient delivery times.

In one aspect, the invention provides a method for radiation therapy treatment using a radiation delivery device. The method includes providing a patient model, dosimetric constraints, delivery motion constraints, and delivery coordinate space of the radiation delivery device, where the delivery coordinate space is represented as a mesh with vertices connected by edges, where the vertices correspond to directions of a beam eye view (BEV) of the radiation delivery device, where each BEV has corresponding area elements resulting from beam collimation. The method also includes constructing BEV region connectivity manifolds from the patient model, the dosimetric constraints, the delivery coordinate space, and existing beam trajectories, wherein each of the BEV region connectivity manifolds represents connections between contiguous 2D target regions, wherein each of the 2D target regions is defined at each of the vertices of the delivery coordinate space. The method includes selecting beam trajectories based on region connectedness information in the BEV region connectivity manifolds, the dosimetric constraints, the delivery motion constraints, and the existing beam trajectories. The method also includes delivering radiation using the radiation delivery device in accordance with the beam trajectories.

The selecting of beam trajectories may also be based on a BEV dose section and a BEV score section, wherein the term "section" refers to a section of a fiber bundle. The selecting of beam trajectories may use a max-distance function to select among trajectories found using a min-distance function. The selecting of beam trajectories may maximize angular spread and minimizes trajectory interference by including in the min-distance function and max-distance function a per-voxel angular flux defined to be the number of unique directions at which the beam hits a given voxel with some spherical binning scheme.

The constructing of the BEV region connectivity manifold may include i) at each vertex, identifying contiguous 2D target regions using a binary selection criterion to identify apertures for treatment, and ii) identifying connections between contiguous 2D target regions of neighboring vertices. The constructing of the BEV region connectivity manifold may include expanding regions whose voxels have low binary angular flux counts, and contracting regions whose voxels have high (non-binary) angular flux counts, wherein the angular flux counts are defined to be the number of unique directions at which the beam hits a given voxel with some spherical binning scheme.

The binary selection criterion may be based on a BEV dose section, a BEV score section, and existing beam trajectories.

The method may also include generating a BEV dose section representing BEV dosimetrics for each area element of the BEV at each vertex in the delivery coordinate space; and generating a BEV score section representing a measure of goodness for treatment at each area element of each vertex in delivery coordinate space.

BRIEF DESCRIPTION OF THE DRAWINGS

FIGS. 2A-C demonstrate MLC aperture contention created by failing to consider MLC synchronization in cases where the optimizer algorithm is presented with a choice of regions to expose. PTV surrounds an OAR axially. In FIG. 2A, human intuition can infer an optimal solution by synchronizing the MLC to remain on the right side of the PTV for the duration of the arc. In FIG. 2B, failure to synchronize the beam-collimating device results in suboptimal trajectories. In FIG. 2C, failure to synchronize adjacent leaf pairs results in a suboptimal trajectory.

FIG. 3 is a flow chart of a method of trajectory optimization according to an embodiment of the present invention.

FIGS. 6A-C are illustrations of a torus delivery coordinate space demonstrating the discontinuities that can arise from cyclic coordinates, according to an embodiment of the invention.

FIG. 7 is a graphical illustration of a region of interest mesh containing a planning target volume and the patient's organs at risk, according to an embodiment of the invention.

FIG. 8A is an illustration of the primary radiation collimating device, according to an embodiment of the invention.

FIGS. 11A-D illustrate storing of BEV score regions as both an array of Boolean pixels, and also as a polygon, according to an embodiment of the invention.

In FIG. 13A, points A and B are included in the same trajectory, resulting from both BEV determining high "goodness". In FIG. 13B, points A and B are determined to be members of separate trajectories, resulting from a multiple region connectivity manifolds.

FIG. 22A is a single strip, which has boundaries on top and bottom, and a cycle around the strip. FIG. 22B is a torus which has no boundary and two fundamental cycles. FIG. 22C is a sphere which has no boundary and no fundamental cycles.

DETAILED DESCRIPTION

Definitions

The term "BEV" or "beam's eye view" refers to a perspective on the patient assumed from the direction of the incident radiation.

The term "MLC" or "multi-leaf collimator" refers to a component of the beam shaping elements of the radiation delivery device.

The term "monitor unit" or "MU" refers to a measurable unit of charge collected by the radiation delivery device and relates to the amount of radiation exiting the radiation delivery device.

The term "volumetric modulated arc therapy" or "VMAT" refers to a technique of irradiating a patient with a delivery device that forms an arc-like trajectory about the patient using a rotating mechanical gantry system.

Overview

FIG. 3 describes the process of generating trajectories with TORUS. The inputs to the algorithm are shown in row 300: The patient's model (ROI—regions of interest), dosimetric constraints, and the delivery coordinate space corresponding to the delivery device and patient configuration. The ROI and dosimetric constraints are used to define the BEV region connectivity manifold in 302. Using this connectivity manifold as a scaffold, a search graph is constructed and path optimization is carried out using a dual-metric optimization technique in 304. The volumetric coverage provided by this new trajectory is then evaluated in 306. If coverage is to be boosted through small aperture adjustments, path 308 is taken. If the current set of trajectories does not provide sufficient coverage, path 310 is taken and an additional trajectory is created. The trajectories are optionally post-processed, e.g. applying B-spline smoothing, in step 312. The final set of radiation trajectories is then output in 314.

Inputs for Radiation Delivery Optimization

Delivery Coordinate Space and Beam Settings

A device that delivers megavoltage radiation for therapeutic intent to a patient shall be referred to as the radiation delivery device. According to some embodiments, the device is constructed by mounting a megavoltage linear accelerator on any one of: 1. a mechanical rotating gantry, 2.

a robotic arm, 3. a rotating slip ring. According to some embodiments the device is constructed by mounting a radioactive material on any of the above mechanical systems. According to some embodiments the device is constructed by transporting protons or ions to a mechanically driven treatment head capable of motion around the patient. Aspects of the present technology relate to the production of megavoltage ionizing radiation for therapeutic purpose.

Figure 1A:
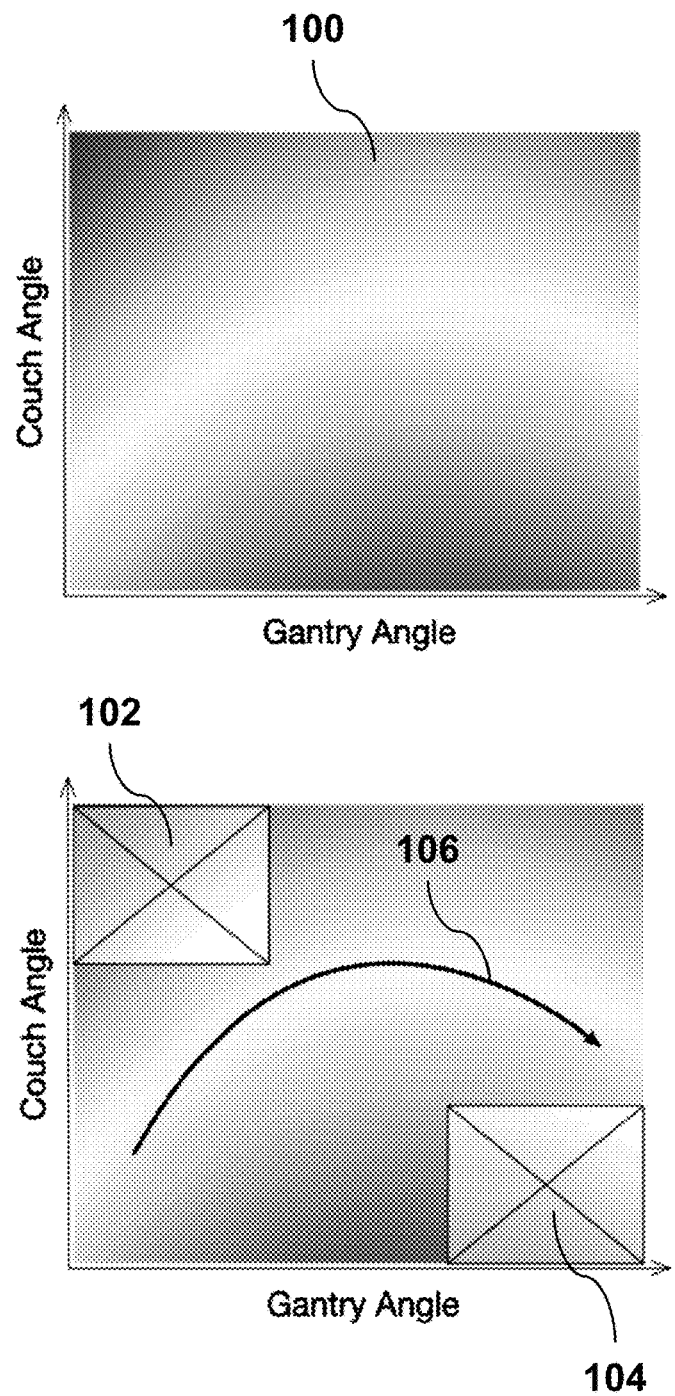
FIG. 1A illustrates a common beam angle optimization approach taken in trajectory optimization using an incident beam-angle-scoring step to create a score map (top) where lighter regions denote higher scores. Collisions are generally marked out for avoidance and then an optimization is performed on this score map (bottom).
Figure 1B:
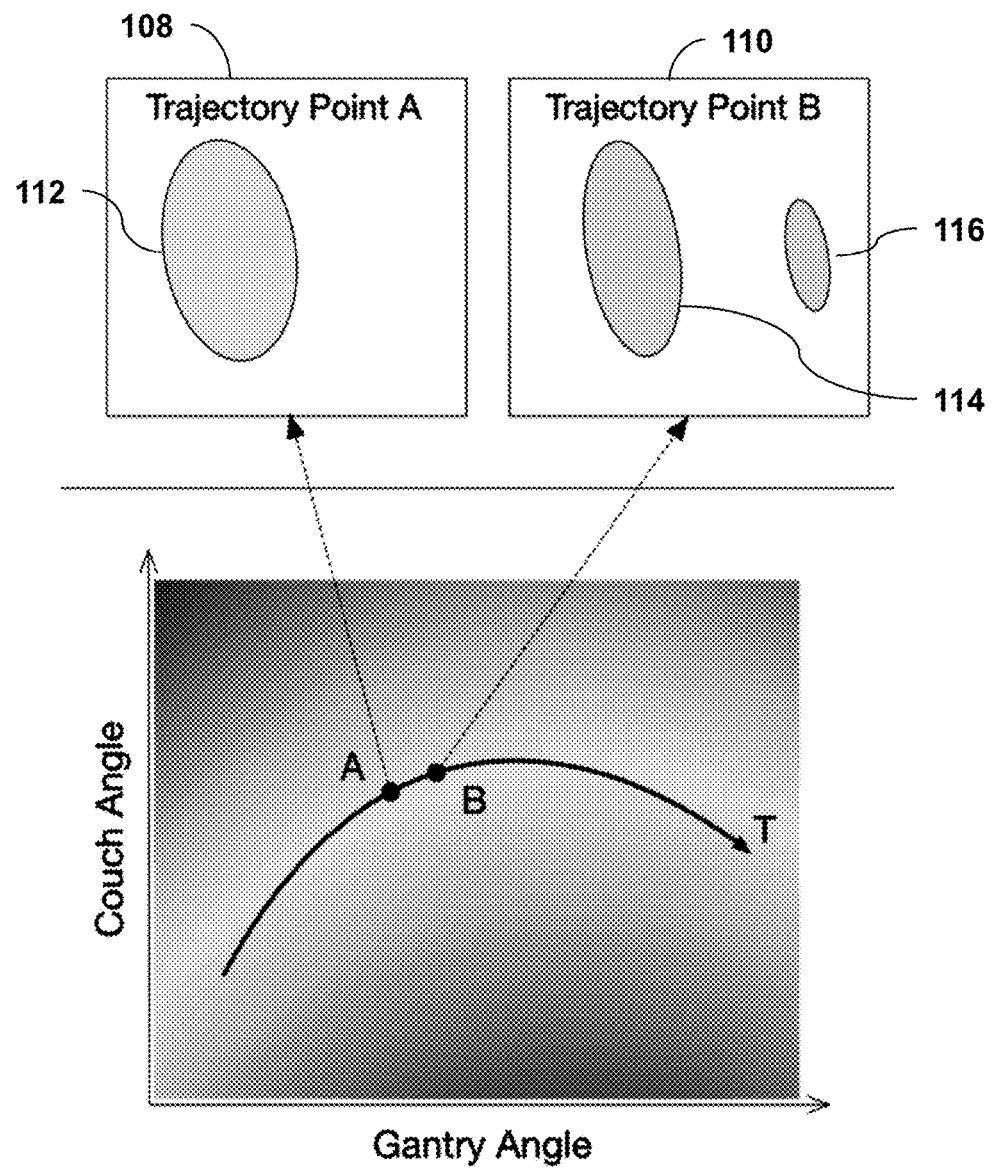
FIG. 1B illustrates an optimal trajectory T derived using the common beam angle optimization approach. Adjacent trajectory points A and B can be evaluated with nearly equivalent "goodness" score yet have substantially uncorrelated optimal apertures. Points A and B are unfit candidates to comprise adjacent points on an optimal trajectory.
Figure 4:
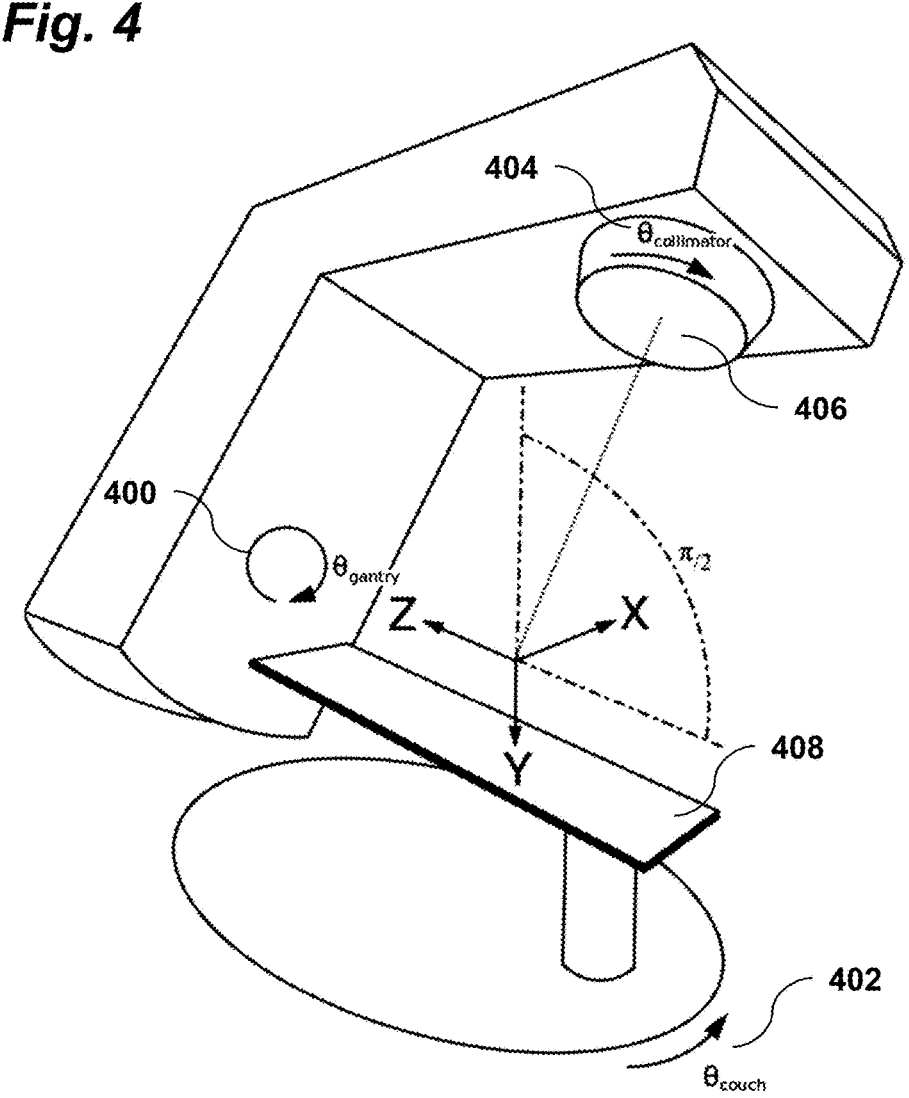
FIG. 4 is a perspective view of a radiation delivery device using a radiation emitting component affixed to a mechanical gantry according to an embodiment of the invention. The radiation emitting device can rotate around the patient on a set of mechanical axes as depicted in the figure.

According to some embodiments, the configuration of the radiation delivery device's mechanical axes is defined by a set of mechanical coordinates. For instance, in the case of a gantry mounted device design, such as in FIG. 4, the location of the treatment head 406 relative to the patient on a couch 408 is parameterized by a gantry angle 400 and patient support couch angle 402, while a collimator angle 404 rotates the treatment head 406 itself. The delivery coordinate space is defined as the set of all allowable mechanical coordinates.

According to some embodiments, the delivery coordinate space is dependent on both the radiation delivery device and an individual patient's anatomy. The radiation delivery device includes variables that parameterize the device's motion and the set of allowable coordinates requires determination based on internal device restrictions such as limitations in mechanical axes. Similarly, based on a patient's anatomy and the intended treatment site, the delivery coordinate space is truncated to avoid collisions between the patient and the radiation delivery device.

According to some embodiments, the motion of the delivery device is described using directional, rotational, and collimating coordinates. Directional coordinates are those that define the physical location and direction of the radiation treatment head relative to the patient (e.g. gantry angle, couch angle, couch translation). Rotational coordinates are those that define the rotation of the delivery device's treatment head about its direction vector (e.g. collimator angle). Collimating coordinates are coordinates describing movable radiation blocking or shielding components used to modify the radiation fluence exiting the delivery device.

According to some embodiments, the delivery coordinate space is defined to consist of directional and rotational coordinates. Since, from a beam's eye view, different rotations are related to one-another by a straightforward rotation, the delivery coordinate space are defined by tuples/points of the form ($\theta_{gantry}$, $\theta_{couch}$, $\theta_{collimator}$=0). In this definition there are two independent variables, hence, the set of allowable points will form a two dimensional manifold.

Figure 5:
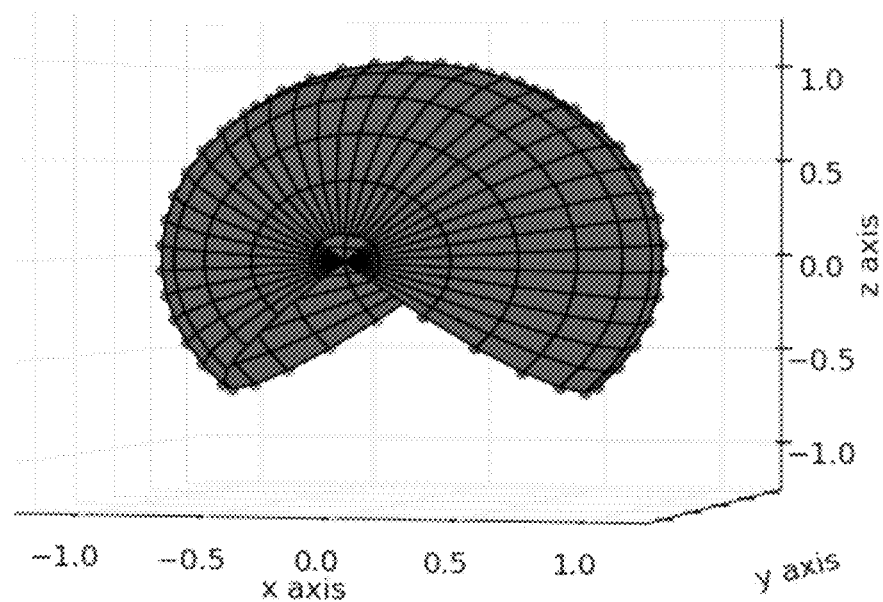
FIG. 5 illustrates a sample delivery coordinate space defined as a mesh comprised of vertices, edges and faces describing the range for which the radiation device may travel, according to an embodiment of the invention.

According to some embodiments, the delivery coordinate space is discretized and the connection of these discrete points is defined. An example is provided where the delivery coordinate space is discretized with a two dimensional (2D) mesh. The 2D mesh is defined by a set of vertices (delivery coordinate points), edges, and faces. In this definition an edge in the delivery coordinate space connects two vertices, and a face is a polygon of 3 or more vertices. For a manifold where the space is of dimension 3 or greater, n-polytopes up to the dimension of the space are required to represent the full delivery coordinate space (polytopization). By using a mesh instead of simply a list of vertices, all topological information is retained, such as dimensionality, connectivity, holes and boundaries. A sample delivery coordinate space is plotted in FIG. 5.

According to some embodiments, a delivery coordinate space is constructed for a radiation delivery device with a mechanical gantry, collimator and patient support couch angle, in which the gantry and couch may travel cyclicly over a 360 degree rotation about a single isocentric point. In this embodiment, the delivery coordinate space takes the form of a topological torus, as shown in FIG. 6C.

According to other embodiments, restricting to 360 degrees of gantry and only 180 degrees of couch angle motion, the space becomes a topological Klein bottle.

According to some embodiments, due to delivery device constraints the angles are limited such that $\theta_{gantry} \in [-180, 180]$ and $\theta_{couch} \in [-90, 90]$, then the space is a rectangle, topologically, the closed disk $D_1$.

According to other embodiments, if the delivery coordinates are spherical angles (polar, azimuth) then the topological space is a sphere, $S^2$.

According to other embodiments, if the delivery coordinates are restricted to be a finite family of constant $\theta_{couch}$ arcs, then the delivery coordinate space is a set of n disjoint $S^1$ circles.

In summary, in the present technology, a delivery coordinate space is defined by:
  Vertices: tuples of ($\theta_{gantry}$, $\theta_{couch}$, $\theta_{collimator}$) angles
  Edges: start and end vertex, and ($\Delta\theta_{gantry}$, $\Delta\theta_{couch}$, $\Delta\theta_{collimator}$) angle changes when moving along edge
  n-polytopes: ordered list of n vertices In the present technology, the importance of storing the connectivity of delivery angles (deltas along edges) can be understood by considering the torus delivery coordinate space described above. Consider a trajectory where a gantry angle increases from 300 to 420 degrees as shown in FIGS. 6A-C. When drawn cyclically such that 360 loops back to 0 degrees, a jump discontinuity appears to exist (FIG. 6A). When this trajectory is plotted on the surface of a torus it can be seen that the curve is continuous (FIG. 6C). For dose calculation purposes, 420 degrees is an equivalent delivery device location to 60 degrees. However, the delivery device may expect specification such as in FIG. 6B, which is entirely equivalent from a BEV point of view but distinct from the point of view of coordinates for the delivery device.

According to some embodiments, the radiation delivery method keeps track of both the vertex in delivery coordinate space, as well as the true coordinate values. FIG. 6A demonstrates how the trajectory moves through delivery coordinate space, while FIG. 6B shows how the true coordinate values change along the trajectory. This approach will allow the delivery coordinate space to be finite in size, while avoiding non-physical jumps in the delivery coordinates. Without storing the angle shifts along the edges, it would be impossible to infer the true delivery coordinate values when passing through cyclic boundaries.

Delivery Device Specifications

In addition to information about which delivery coordinates are possible, according to some embodiments delivery device specifications are defined to include the maximum travel velocity and acceleration of each delivery coordinate. These are used to control the mechanical velocity of the radiation delivery device for each delivery coordinate as well as the velocity limitations of the device.

Once the delivery device specifications are specified, the delivery coordinate space can be built by following the logic:
  Specify delivery device→define initial delivery coordinate space
  Truncate space based on delivery device specifications (e.g. if static patient couch required, remove edges/faces that have nonzero $\Delta\theta_{couch}$)
  Truncate space based on patient anatomy (avoid collisions between patient and device or undefined or non-imaged regions of the patient anatomy)

Delivery Motion Constraints

According to some embodiments, the radiation delivery method is required to limit or restrict the motion of the delivery device to minimize patient motion or dynamic motion of a delivery coordinate during a treatment. For instance it may be a operator requirement to deliver only radiation treatments with constant couch and constant collimator. The method of radiation delivery is designed to allow the operator control over the delivery coordinate space and limitations in the dynamic motion of a delivery coordinate.

To provide an example, an operator-specified limit of non-dynamic collimator motion is implemented in the trajectory graph optimization by only allowing nodes to connect to other nodes with the same collimator value.

According to some embodiments, the radiation delivery method allows definition of non-coplanar delivery trajectories with one or more independent trajectories. In this case all trajectories are permitted to search the entire delivery coordinate space with edges of nonzero $\Delta\theta_{couch}$ removed. In the case of a dynamic patient support couch, no further truncation of the delivery coordinate space is required.

According to some embodiments, delivery motion constraints include the number of trajectories to deliver.

According to some embodiments, delivery motion constraints include the allowance for translation of the radiation isocenter throughout the delivery.

Any strategy of truncating/modifying the delivery coordinate space and/or the rotational delivery coordinates to restrict the allowed motion of trajectories from the full set of possible trajectories falls under the classification delivery motion constraints.

According to some embodiments, an operator input for delivery motion constraints is defined through elements of a graphical user interface such as adjusting a slider bar or other graphical element to adjust the delivery motion constraints.

Patient Model

According to some embodiments, the patient model used in the formation of the radiation delivery device's trajectory may consist of two elements: a physical density map, and regions of interest. The physical density map is a 3D (or 4D if time is considered) map of density that is used for doing dose calculations.

A region of interest (ROI) is a 3D (or 4D in the case of 4D treatments) defined region occupied by some part of the patient that is clinically relevant for the treatment. ROI can be divided into three classes: planning target volume (PTV), organs at risk (OAR), and the patient's body. According to some embodiments, these 3D voxel structures are converted into triangle meshes due to the ease of transforming meshes between coordinate systems. FIG. 7 shows an example of 3D triangle meshes of ROI. The triangles are sufficiently small that the global surface appears smooth. 700 is the surrounding PTV mesh, 702 and 704 are lung ROI, 706 is the spinal cord ROI, 708 is the heart ROI, and 710 is the liver ROI.

Complications may arise when ROI overlap and points can be inside multiple ROI at once. Therefore, according to some embodiments it is necessary to ensure every point is in exactly 0 (outside patient) or 1 ROI. Such a tie-breaking condition is also stored as a member of the patient model.

Dosimetric Constraints

According to some embodiments, dosimetric constraints are used to control radiation dose levels. Constraint types include maximum, minimum, mean, median dose as well as absolute/relative volumes receiving a dose level. Each constraint type can be specified as an upper or lower limit to allow definition of targets or avoidances.

According to some embodiments, dosimetric constraints are defined for all PTV and ROI in the patient model with priorities for each limit.

According to some embodiments, dosimetric constraints also include definitions of desired dose gradients to be delivered by the radiation device.

BEV Sectioning

Aspects of the present technology relate to three important data structures which record information from a beam's eye view (BEV) perspective of the patient's anatomy: BEV dose bundle section, BEV score bundle section, and BEV region connectivity manifold.

BEV Dose Bundle Section

According to some embodiments, a point in delivery coordinate space defines a physical location of the radiation device's treatment head. The radiation delivery device emits radiation from a point (called the source), and it passes through collimating devices in the treatment head to shape a radiation field. The primary component (non-scatter) of radiation coming out of the treatment head follow approximately rays emitting out from the radiation source. By defining a plane, the BEV plane, at some distance from the radiation source perpendicular to some preferred beam ray (typically the ray down the central axis), rays can be classified by 2D coordinates.

Figure 8B:
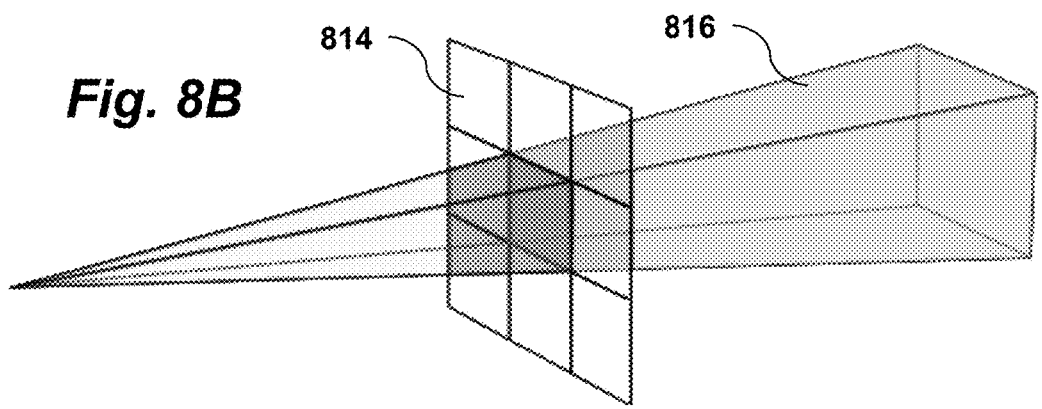
FIG. 8B illustrates division of the radiation field into beam's eye view area elements (beamlets), according to an embodiment of the invention. In this example the beam's eye view plane is divided into 9 beamlets.

To discretize this information the BEV plane can be broken down into BEV area elements which partition the plane (in practice these usually comprise a rectangular set of pixels) and dose and geometric information about ROI along each of these BEV area elements (beamlets) can be considered. The concept is illustrated in FIG. 8A and FIG. 8B. FIG. 8B shows that the BEV plane 814 is divided into 9 area elements, with the rectangular pyramid 816 representing a beamlet corresponding to the central beamlet. In FIG. 8A, 800 is the radiation source, 802 and 804 are upper jaws, 806 and 808 are lower jaws, 810 are the multileaf collimators, and 812 is the collimated radiation beam.

According to some embodiments, the BEV point of view is taken advantage of by storing dose information in the following way. The BEV plane is discretized into a 2D array as shown to the above with size ($N_x$, $N_y$), with the generalization to arbitrary BEV area elements trivial by replacing the 2 indexes $n_x$ and $n_y$ with a single index $n_{beamlet}$ that arbitrarily enumerates the area elements as in the following discussion. Each area element on this 2D grid represents a single beamlet. To probe all possible beamlets, collimation devices are assumed to be completely open and the dose intensity of the beamlets are set to be uniform (arbitrarily set to 1.0).

According to some embodiments, each beamlet is used in a calculation of absorbed dose in the patient model. The 3D dose distribution is processed to determine dose statistics to each ROI, such as minimum, maximum, and average dose, and volume integrated dose, and these statistics are stored in the beamlet's corresponding area element.

According to some embodiments, if there are $N_{statistics}$ dose statistics used, then the BEV dose bundle section is a 5D array of size ($N_{vertex}$, $N_x$, $N_y$, $N_{ROI}$, $N_{statistics}$). Each vertex gives a single BEV, each BEV is discretized into a 2D array of beamlets ($N_x$, $N_y$), and $N_{statistics}$ dose statistics are stored for each of $N_{ROI}$ regions of interest.

According to some embodiments, the BEV dose bundle section can be considered a 4D array of size ($N_{vertex}$, $N_x$, $N_y$, $N_{ROI}$). The value of the BEV dose bundle section at index ($n_{vertex}$, $n_x$, $n_y$, $n_{ROI}$) is therefore given by the volume-integrated dose $$D_{n_{vertex},n_x,n_y,n_{ROI}} = \int dx\,dy\,dz\, D_{n_{ROI}}(x,y,z)$$

where $D_{n_{ROI}}(x, y, z)$ is the dose to this ROI at (x, y, z) in the patient volume.

Figure 9A:
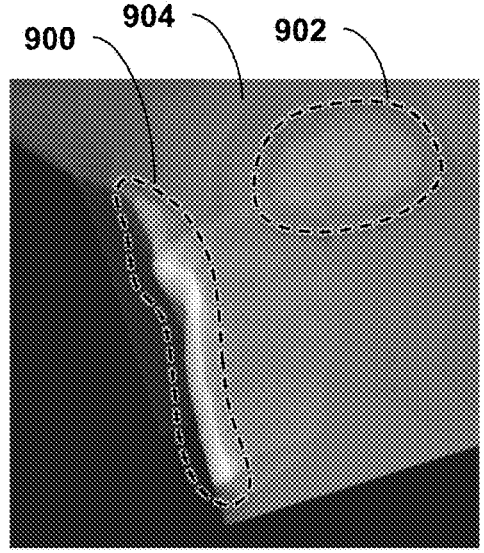
FIG. 9A is a 2-dimensional representation of a dose bundle section as calculated for a single vertex on a delivery coordinate manifold, according to an embodiment of the invention.

Shown in FIG. 9A is a 2D representation of a BEV dose bundle section, calculated for a single vertex. In this example, PTV dose 900, OAR dose 902, and other body tissue 904 are shown. It can be seen that on the left side of the patient from this BEV is a light region, which is indicating a preferential region through which to expose the PTV.

Since a BEV dose bundle section stores BEV dose information for each vertex on the delivery coordinate space, it inherits information from the delivery coordinate space about how the BEV dose distributions change as a trajectory moves through the delivery coordinate space (i.e. when the treatment head is moving).

BEV Score Bundle Section

Aspects of the current technology relate to a BEV score bundle section, which is a contraction of the 5D BEV dose bundle section into a 3D matrix of data of size ($N_{vertex}$, $N_x$, $N_y$), where each value is a measure of the "goodness" of the given beamlet for each vertex. The score combines all information about the ROI dosimetrics for each beamlet in each delivery coordinate point into a single number. In its most general definition, the score at index ($n_{vertex}$, $n_x$, $n_y$) is any function of the BEV dose bundle section D at indexes ($n_{vertex}$, $n_x$, $n_y$, i, j) where i runs over all ROI and j runs over all dose statistics. According to some embodiments, a requirement is imposed ensuring the function gives greater scores for preferential beamlets through which to expose the PTV.

The mathematical form of the score function can vary and depends on the specific implementation of the invention. According to some embodiments, the score uses dosimetric constraints specified in the patient prescription alongside dose statistics of the beamlets. For instance, beam's eye view dosimetrics (BEVD) can be used to score beamlets.

According to some embodiments, the use of fluence optimization from all possible vertices, formulating a convex problem, in which beamlet intensities may be used as a "score".

According to some embodiments, a single dose statistic, the volume-integrated dose, may be used and the score defined to be a linear combination of the ROI volume integrated doses for each beamlet and vertex. In this case the score at index ($n_{vertex}$, $n_x$, $n_y$) is defined to be:

$$S_{n_{vertex},n_x,n_y} = \Sigma C_{n_{ROI}} D_{n_{vertex},n_x,n_y,n_{ROI}}$$

The coefficients $C_i$ above are weights for each ROI used to define their importance in the optimization problem.

Figure 9B:
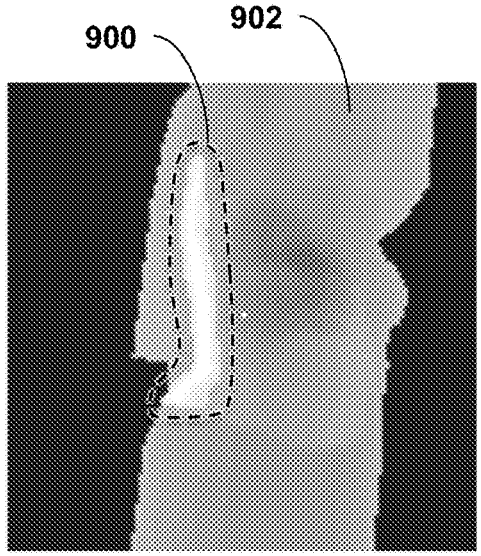
FIG. 9B is a 2-dimensional representation of a score bundle section as calculated for a single vertex on a delivery coordinate manifold, according to an embodiment of the invention.

Shown in FIG. 9B, is an example of beamlet scores from an example BEV. Darker colors are low score, brighter colors high score. The hue also changes from red to green past some score threshold.

According to some embodiments, coefficients $C_i$ may be chosen either on a patient by patient basis, either by explicitly allowing an operator to set the coefficients, by using prior operator knowledge of good choices of coefficients based on the type of treatment required, or by analyzing the dose bundle section to intelligently select coefficients which reflect the geometry of the patient's anatomy.

BEV Region Connectivity Manifold

Aspects of the present technology relate to construction of a BEV region connectivity manifold. According to some embodiments, the information contained in the BEV dose bundle section and BEV score bundle section is applied in a binary selection procedure to determine if a given beamlet at a given vertex is preferential for treatment. For each BEV, the set of preferential pixels form regions, or contiguous sets of pixels. A second step then determines the degree to which these regions connect to other regions in neighboring vertices. The resulting structure of regions and their connectivity is called a BEV region connectivity manifold.

Region Selection Criterion

Given a BEV dose bundle section of size ($N_{vertex}$, $N_x$, $N_y$, $N_{ROI}$, $N_{statistics}$) and a BEV score bundle section of size ($N_{vertex}$, $N_x$, $N_y$), aspects of the present technology relate to determination of whether a given beamlet with index ($n_{vertex}$, $n_x$, $n_y$) qualifies as a preferential candidate in the delivery. This binary selection procedure is referred to as the region selection criterion. According to some embodiments, the region selection criterion is constructed such that a set of preferential beamlets sufficient to adequately expose the PTV is selected without excessively exposing the OAR and/or patient's body outside of the PTV.

According to some embodiments, the region selection criterion may be constructed to be a function of both the BEV dose and score bundle sections. In other words, the region selection criterion includes both local and global information, and so in its most general form is a Boolean function of the form $$R_{n_{vertex},n_x,n_y} = f(n_{vertex}, n_x, n_y, D, S)$$

where D and S represent the BEV dose and score bundle sections.

According to some embodiments of the invention a hybrid approach may be used using information of the potential dose to the entire body and score sections to determine a threshold score value $S_{threshold}$, which is then used only locally. This example of a region selection criterion is defined to be $$f(n_{vertex}, n_x, n_y, D, S) = (S_{n_{vertex},n_x,n_y} > S_{threshold}(D,S))$$
$$\wedge\, (\exists n_{ROI} \in N_{PTV} \text{ such that } D_{n_{vertex},n_x,n_y,n_{ROI}} > 0)$$

where $N_{PTV}$ is the set of all ROI indexes for PTVs. This criterion can be further stated as: the score must be above the score threshold value, and the beamlet must intersect the PTV. The mathematical problem is now reduced to finding a good algorithm for determining for the threshold. According to some embodiments, a BEV dose histogram may be constructed and a BEV score histogram may be used to determine the threshold as follows.

According to some embodiments, a BEV PTV dose histogram may be calculated as follows:

For each ($n_{vertex}$, $n_x$, $n_y$) calculate the total PTV dose:

$$D_{n_{vertex},n_x,n_y}^{PTV} = \Sigma D_{n_{vertex},n_x,n_y,n_{ROI}}$$

Determine the maximum such dose, max ($D_{n_{vertex},n_x,n_y}^{PTV}$) and create $N_{bins}$ bins from 0 up to this maximum. These are called differential histogram bins and are denoted $\partial B_{n_{bin}}^{D}$.

Initialize each bin value $\partial B_{n_{bin}}^{D}$ to zero for $n_{bin}$ between 0 and $N_{bins}-1$.

Loop through each ($n_{vertex}$, $n_x$, $n_y$), and if $D_{n_{vertex},n_x,n_y}^{PTV} > 0$ increment the corresponding bin by 1.

The integrated histogram bins are defined as $B_{n_{bin}}^{D} = \Sigma \partial B_{n}^{D}$ Normalize the differential and integrated histogram bins such that the largest value is 1.0.

Figure 10:
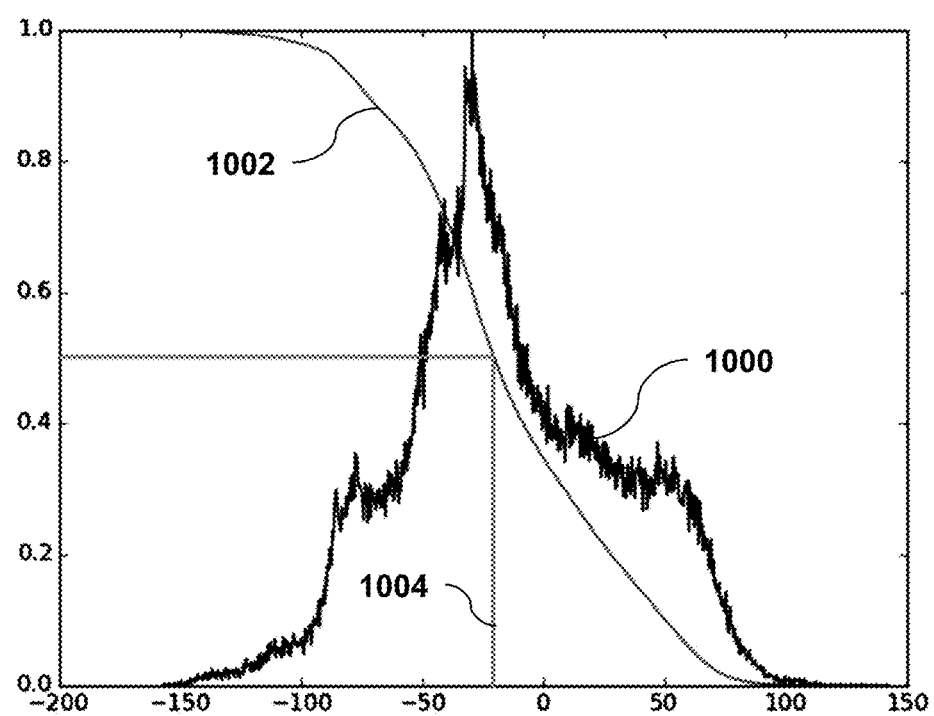
FIG. 10 is a graph showing differential and integrated BEV PTV histograms used for determining a threshold score for preferred candidate beamlets to consider for exposing the planning target volume, according to an embodiment of the invention.

An example of such differential 1000 and integrated 1002 BEV PTV histograms is shown in FIG. 10. This histogram is used to determine a temporary PTV threshold by selecting the PTV dose value $D_{threshold}^{PTV}$ 1004 such that the corresponding value of the integrated histogram at that point is 0.5. Selecting beamlets that have PTV dose above this threshold selects out the top 50% of beamlets that expose the PTV and minimize dose to OAR and body regions.

According to some embodiments, a thresholded BEV score histogram may be calculated as follows.

Define the set of thresholded beamlets as tuples ($n_{vertex}$, $n_x$, $n_y$) such that $D_{n_{vertex},n_x,n_y}^{PTV} > D_{threshold}^{PTV}$ and denote set as $N_{PTV>threshold}$ Calculate maximum max ($S_{n_{vertex},n_x,n_y}$ ∀($n_{vertex}$, $n_x$, $n_y$)∈$N_{PTV>threshold}$) and create $N_{bins}$ bins from 0 up to this maximum. These are the differential histogram bins denoted $\partial B_{n_{bin}}^S$.

Initialize each bin value $\partial B_{n_{bin}}^S$ to zero for $n_{bin}$ between 0 and $N_{bins}-1$.

Loop through each ($n_{vertex}$, $n_x$, $n_y$) in $N_{PTV>threshold}$, and increment the bin corresponding to the score $S_{n_{vertex},n_x,n_y}$.

The integrated histogram bins are defined as $B_{n_{bin}}^S = \Sigma \partial B_n^S$ Normalize the differential and integrated histogram bins such that the largest value is 1.0.

The score threshold value can then determined from this BEV score histogram by selecting the value of score such that the ratio $B^S(S)/[(S-S_{min})/(S_{max}-S_{min})]$ is 0.7, where $B^S(S)$ denotes the integrated histogram height at score value S (i.e. $B_{n_{bin}}^S$ where $n_{bin}$ is the corresponding bin index). Instead of using the value of the histogram height, the ratio of the sides of the rectangle formed by the axes and the green line in the above figure may be used in the selection process. The resulting score threshold will be denoted $S_{threshold}$ representing the value used in the region selection criterion introduced above.

According to some embodiments, region selection is implemented in the following way using the a region value defined as $RV_{n_{vertex},n_x,n_y} = (S_{n_{vertex},n_x,n_y} - S_{threshold})/\max(S)$ $RV_{n_{vertex},n_x,n_y} = -\infty$ unless $\exists n_{ROI} \in N_{PTV}$ such that $D_{n_{vertex},n_x,n_y,n_{ROI}} > 0$ with values between 0 and 1 for beamlets identified as regions, and less than 0 for those which are not.

In FIG. 11A, an example of score values is shown for a given BEV, showing the pixels that pass the region selection criterion. In this image it can be seen that there are two disconnected regions 1002 and 1004 of pixel groups. Each such group of contiguous pixels is called a region (potential sub-apertures for treatment), and these form the building blocks of the BEV region connectivity manifold.

Aspects of the present technology relate to the storing of regions as both an array of Boolean pixels, and also as a polygon, as shown on the right. A polygon consists of an exterior ring of points, and 0 or more interior rings.

According to some embodiments, the exterior and interior rings of each region can be determined using a marching squares algorithm, the result of which is illustrated in FIG. 11B in which dark shaded pixels 1106 are those which pass the region selection criterion, and the outer encompassing polygon 1108 is the exterior ring, and this region has one interior ring 1110 also shown. The advantage of using polygons to store region information is that regions are rotated by applying a rotation matrix to each point, whereas rotation of an image is a more involved calculation. This allows regions at neighboring vertices in the delivery coordinate space to be quickly compared.

Region Connectivity

According to some embodiments, regions at neighboring vertices are connected in the delivery coordinate space to form a BEV region connectivity manifold. This connectivity describes how these regions change, appear, and vanish as one moves along the delivery coordinate space in all directions.

In FIGS. 11C-D, example BEV score distributions are shown with the regions identified as green for two neighboring vertices connected by an edge in the delivery coordinate space. A region is visible on the left and right side of the patient for each image. Overlaying these two images on top of each other, the two left regions coincide and the two right regions coincide with each other. This means that moving along this edge in delivery coordinate space that the left regions are connected, and the right regions are connected, but they do not cross over. The set of all regions and all connections along delivery coordinate space edges form the BEV region connectivity manifold.

Figure 12:
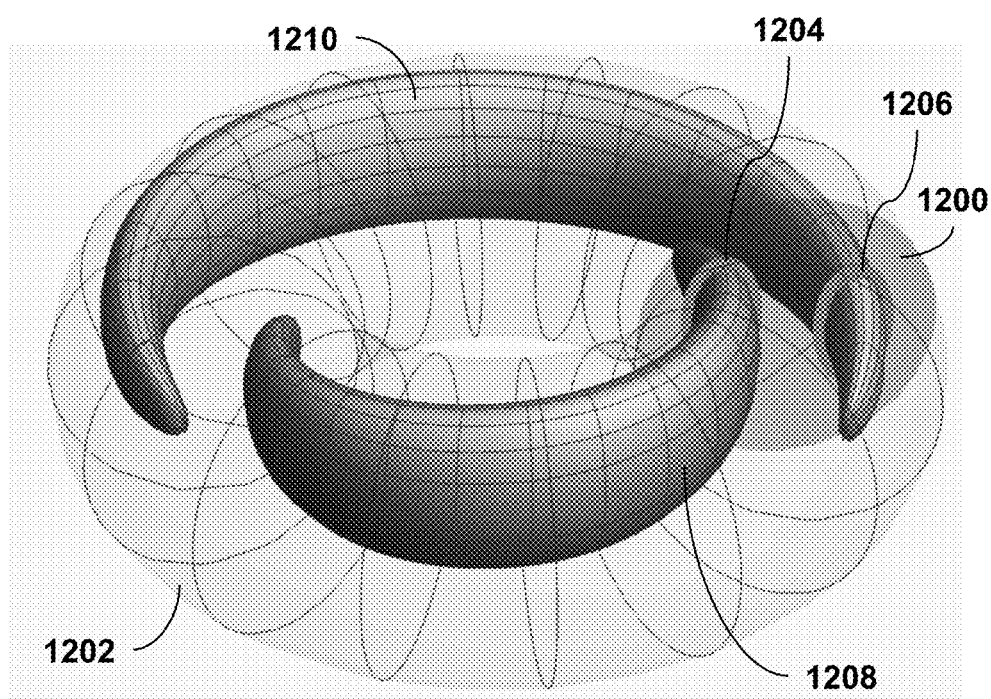
FIG. 12 illustrates a possible BEV region connectivity manifold with 2 separate connected components. A circular disk indicates a sample BEV from a given delivery coordinate direction, according to an embodiment of the invention.

To further illustrate the definition and concept of the BEV region connectivity manifold, a simplified example is used in which the delivery coordinate space has a single degree of freedoms, such as a cyclic gantry coordinate. In this example, the delivery coordinate space can be represented as a circle. When including an additional 2 dimensions (x and y) introduced by the BEV, the BEV score bundle section can be understood to be a 3D object. If each BEV image is drawn as a disk, then drawing a disk for each point in a circle (each representing a single gantry angle) results in a donut-like shape (a solid torus). Rotation around the center of the torus corresponds to rotating gantry angle, and each slice of the torus is a single BEV image from the corresponding direction. Considering each point to be transparent if failing the region selection criterion, and opaque when it passes, then shown in FIG. 12 is a visualization of one possible BEV region connectivity manifold. The slice 1200 through the solid torus 1202 has two disconnected regions 1204, 1206. As the gantry angle rotates, the shape traced out by the "left" regions and the "right" regions form elongated solid shapes 1208, 1210 within the solid torus.

The above example required only 3 dimensions to draw, but in the case where the delivery coordinate space is 2 dimensional drawing the BEV region connectivity manifold accurately would require 4 dimensions.

According to some embodiments, the manifold is represented in the computer in the following way:

Each region is indexed by two numbers ($n_{vertex}$, $n_{subindex}$). The second index $n_{subindex}$ is needed because there can be more than one region per vertex, as seen above where there are left and right regions. The connections between regions are represented by a sparse matrix (called a transition matrix) of zeros and ones $T_{r_1,r_2}$ where $r_1$ and $r_2$ are region multi-indexes of the form ($n_{vertex}$, $n_{subindex}$).

The matrix is initialized to zero and then filled as follows:

Loop over all delivery coordinate space edges, getting pairs of vertices with indexes $v_1$ and $v_2$.

Rotate the regions at vertex $v_1$ by $\Delta\theta_{collimator}$ to align with the regions at vertex $v_2$.

For each region $r_1$ at the first vertex and each region $r_2$ at the second vertex, set $T_{r_1,r_2}$ and $T_{r_2,r_1}$ to 1 if the pair of regions overlap.

According to some embodiments, instead of using overlap of regions, correlation between regions is used to determine region connectivity.

Figures 13A, 13B:
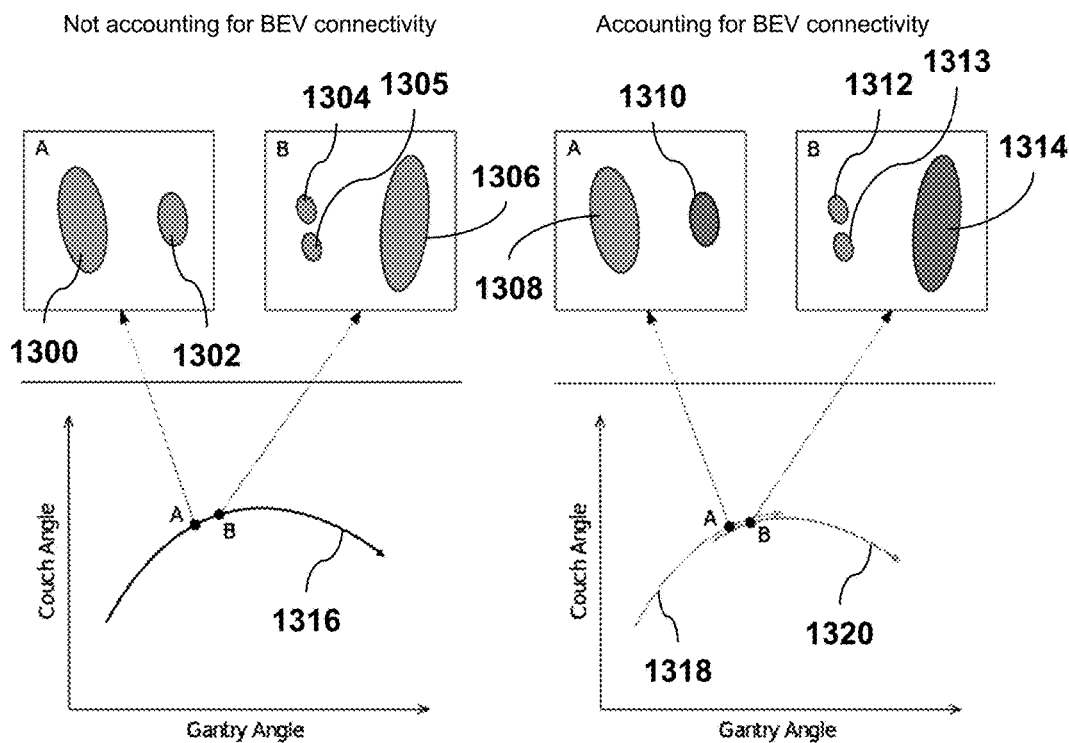
FIGS. 13A-B illustrate how formation of region connectivity manifolds based on aspects of the present technology lead to modified radiation device trajectories, according to an embodiment of the invention.

Aspects of the present technology relates to the preservation of information within each BEV that is not collapsed into a single score. For example, in the solid torus example illustrated in FIG. 12, it can be seen that there are two distinct connected regions 1208, 1210 in the BEV region connectivity manifold and these region manifolds result in two separate trajectories of the radiation device. Because, in the current technology, BEV information is retained (FIG. 13B), it can be seen that a two arc radiation delivery trajectory can expose all regions completely, without having unnecessary exposure to OAR compared to FIG. 13A. In FIG. 13A 1300 and 1302 are disconnected regions at point A of trajectory 1316. At point B of trajectory 1316 there are 3 regions at 1304, 1305, and 1306. When region connectivity is considered the trajectory of FIG. 13A is broken down into trajectories 1318 and 1320 in FIG. 13B. Apertures 1308, 1312, 1313 are part of the connected component corresponding to trajectory 1318, while apertures 1310 and 1314 correspond to trajectory 1320.

Trajectory Optimization of the Radiation Delivery Device

This section describes how the information stored in the BEV dose bundle section, BEV score bundle section, and BEV region connectivity manifolds are used to generate radiotherapy plans for treatment. A key aspect of the technology is the role of BEV region connectivity manifolds in guiding the optimizer. Because of the definition of scores and regions, the optimizer has information on which beamlets are preferential to treat the PTV while avoiding OAR. This knowledge reduces the size of the search space compared to other optimization approaches, enabling path optimization techniques to be very effective.

Optimization Overview

A fundamental assumption is made in the present technology, that optimal treatment trajectories are those that expose the PTV as much as possible while avoiding OAR, enter the patient from many different directions to allow the dose to focus more strongly in the PTV, and finish in a short delivery time. The latter is in conflict with the former and middle goals. For instance, a plan with an optimal dose distribution would be one that enters from every direction with a high degree of MLC modulation and shielding to achieve an optimal fluence; however such a trajectory would take an excessive amount of time to deliver, and further the large MUs involved would cause the low-dose build up to be significant. Therefore, it is important to balance the solid angle that a trajectory covers around the patient, but in an efficient delivery time. The optimization algorithm must find a solution that "maximizes" the solid angle spread (long trajectories), but does so using relatively "straight" trajectories. A geodesic is a shortest possible path between two points on a sphere, and so accurately captures the idea of "straightness" required in delivering a trajectory from point A to point B. Lastly, the goal of having "long" trajectories can be achieved by using starting and ending points that are far away.

A geodesic is calculated by determining the line that minimizes a distance function between two points on a sphere. In the context of radiotherapy trajectory optimization, it is desirable for trajectories to traverse control points having regions with high score. To guide the geodesic to select such trajectories it is necessary to define a distance function such that smaller distances (but non-negative) are given by favorable paths.

In order to choose "long" trajectories, it is necessary to evaluate the length of a trajectory by using a distance function where larger distances are favorable. This means that to overcome the conflict between trying to find "short" but "long" trajectories, it is necessary to use two distance functions having different meanings and roles in the optimization. Aspects of the present technology relate to the optimization of such "short" but "long" trajectories.

Figure 14:
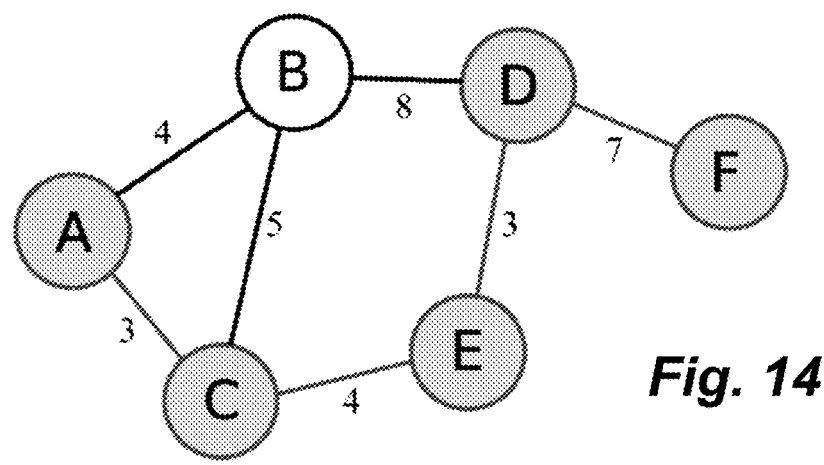
FIG. 14 illustrates a graph optimization problem, according to an embodiment of the invention. Numbers on the lines connecting the circular nodes represent distances, and the shortest path from A to F is given by the shaded circles.

According to some embodiments, the concept is translated into a computer algorithm by using modified path optimization techniques on graphs. A graph is a set of nodes, and edges that connect nodes and contain distance information. A path is a finite sequence of edges that connect a sequence of nodes. An optimization algorithm searches this graph, looking for the shortest path between two given nodes. Shown in FIG. 14 is a graph with 6 nodes labeled A through F. In this example, the shortest path between nodes A and F is given by the shaded path, A-C-E-D-F.

According to some embodiments, since shortest path optimization algorithms look for a path that minimizes distance, but that tend to pass through "good" regions, a min-distance function is used where smaller non-negative values are assigned to better edges. When selecting long paths that cover a large solid angle, a max-distance function is used where larger distances are better. Roughly speaking these functions obey:

max-distance="goodness"
min-distance=1/"goodness"

According to some embodiments, the total min/max-distance of a path is given as the sum of min/max-distances of each edge, but can also be defined as a function of the entire path.

According to some embodiments, these two distance functions are combined in one algorithm as follows: First a set of nodes corresponding to control points is created, and edges between these control points are introduced by considering motion between control points. Then a modified Dijkstra shortest path optimization algorithm is run using the min-distance function to find the shortest path from a set of starting nodes on the boundary of each connected component in the BEV region connectivity manifold to find the shortest path to all other accessible boundary points from each starting point. Finally, the path with the largest max-distance is selected, and the corresponding radiotherapy plan trajectory is created.

Trajectory and Graph Definitions

A radiotherapy plan consists of a list of control points, which will be represented as nodes in the search graph. Each control point is a single moment of the treatment, and is defined by specifying:

Directional, rotational, and collimating delivery coordinates

Dose rate

According to some embodiments, the directional coordinates are fixed by specifying the vertex in the delivery coordinate space. Similarly, the rotational coordinate (for example collimator angle) can be determined by discretizing all possible collimator angles, either between a minimum and maximum value or cyclically between 0 and 360 degrees, and choosing a collimator index to pick one of these discrete values.

Figure 15:
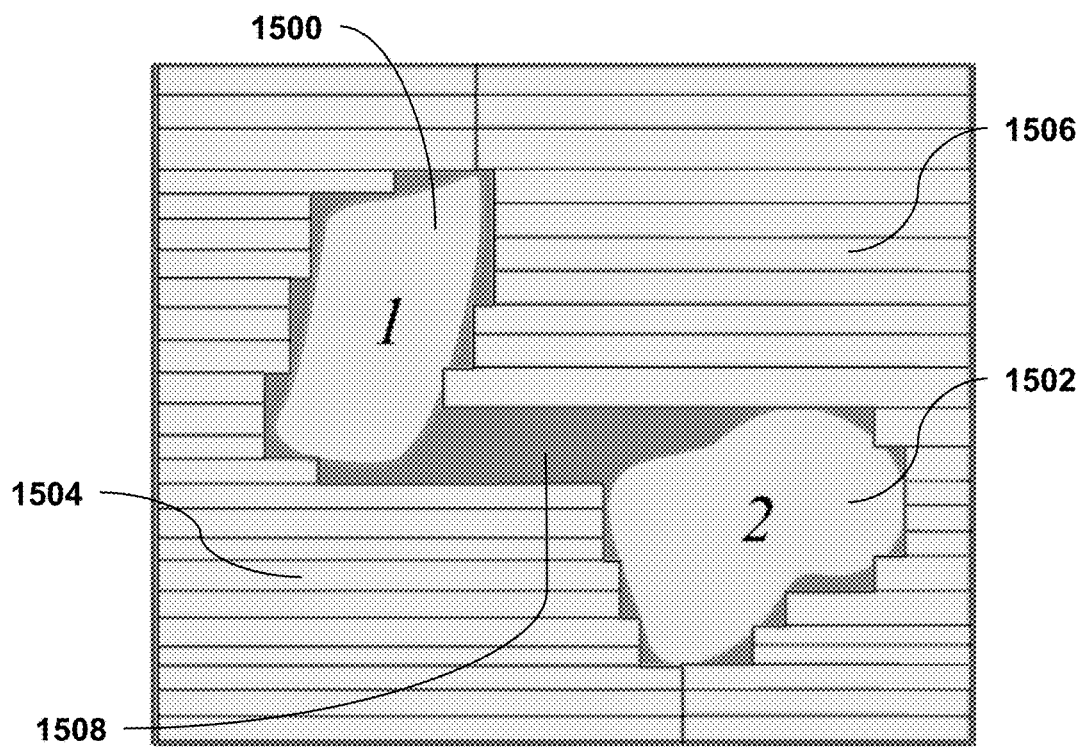
FIG. 15 illustrates MLC fitting to regions, according to an embodiment of the invention. The MLC aperture is as closed as possible while completely exposing region 1 and 2. MLC contention causes some unwanted exposure of the dark region between the two regions.

According to some embodiments, nodes are constructed so that each node uniquely specifies the collimating delivery coordinates. Each node specifies which regions are treated, and the collimating delivery coordinates are then inferred from this. For example, if at a given beam position (vertex) and for a given collimator angle there are two regions 1500, 1502 as shown in FIG. 15, and the node specifies that both are to be treated, then the MLC aperture (left bank of leaves in 1504 and right bank of leaves in 1506) is configured so that it is as closed as possible while leaving these areas exposed. This condition can lead to cases where there are areas of pixels which did not pass the region selection criterion that are exposed, such as area 1508, depending on the shapes of the regions and the collimator angle. According to some embodiments, unwanted exposure of regions from poorly fitted collimation is penalized in the distance function.

According to some embodiments, the choice of regions to expose are represented by using a region bitfield, a binary number, a sequence of 0s and 1s, with 1 meaning that the respective region is selected.

Figure 16:
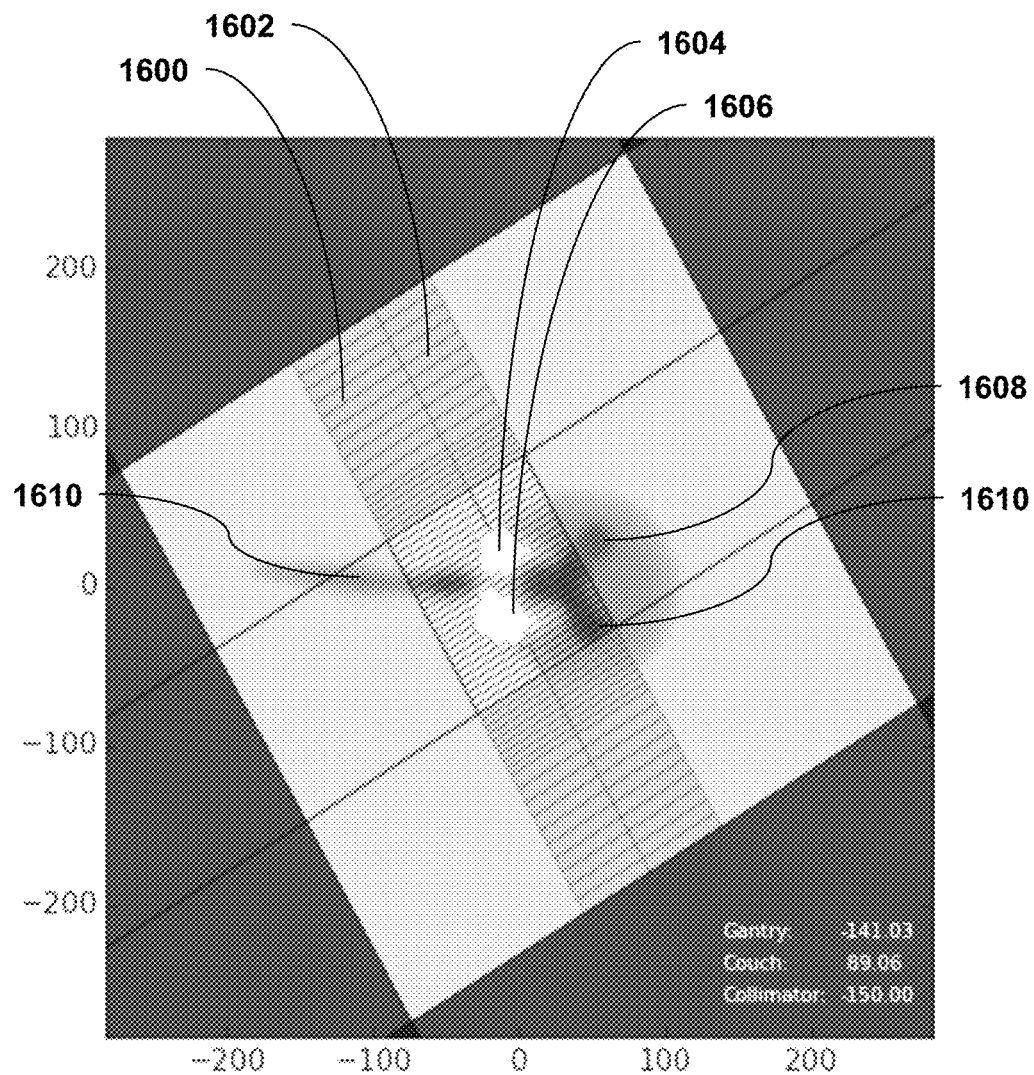
FIG. 16 is a BEV representation of beamlet scores (light and dark background regions) with overlaying MLC leaves exposing two separate light regions with high score, according to an embodiment of the invention.

According to some embodiments, these three integers, vertex, collimator index, and region bitfield, determine uniquely the control point, and so constitute the node in search graph. Shown in FIG. 16 is an example of what a control point can look like for one such node. A control point is a term used to describe an single instant during a continuous treatment, and so is represented by the gantry, couch, collimator angles and jaw and MLC positions. The vertical and horizontal axes represent x and y distance at the BEV plane in mm. 1600 and 1602 are the left and right banks of MLCs, and 1604 and 1606 are two regions of open MLCs exposing the bright high scoring regions. 1608 and 1610 are low score dark regions corresponding with patient eyes, and 1610 that corresponding to spinal cord.

According to some embodiments, dose rate information is stored in the graph.

Shortest Distance Path Optimization
Constructing the Graph

According to some embodiments, a combination of vertex, collimator index, region bitfield uniquely identify each node, and each node is associated with a single possible control point. This section discusses how edges in the graph are defined. Computationally, it is not necessary to generate the entire graph before optimizing; nodes and edges can be generated dynamically during the optimization. This can be useful because distances on edges that are never hit are never calculated, and it might be that, in the case of cyclic collimator, the graph is technically infinite in size.

According to some embodiments, a rule can be defined which determines if an edge between two nodes exists. Given two nodes $N_1=(v_1, c_1, b_1)$ and $N_2=(v_2, c_2, b_2)$, there is an edge E connecting $N_1$ to $N_2$ if the following rules are satisfied:

There is an edge e ending on vertex $v_1$ and $v_2$ in the delivery coordinate space For edge e, calculate the time for the delivery device to move through the directional delivery coordinates by ($\Delta\theta_{gantry}$, $\Delta\theta_{couch}$). This is calculated by using the delivery device's maximum speeds along each delivery coordinate and taking the maximum of the times, $\Delta t_{directional}=\max(\Delta t_{gantry}, \Delta t_{couch})$. Given $\Delta\theta_{collimator}=\theta_{collimator}(c_2)-\theta_{collimator}(c_1)$, the collimators can be connected by an edge if $\Delta t_{collimator}<\Delta t_{directional}$.

The region bitfields $b_1$ and $b_2$ must satisfy the following property. Let $\{r_{1,i}\}$ be the regions corresponding to bitfield $b_1$, and similarly for $\{r_{2,i}\}$. Then all of these regions must live in the same connected component of the BEV region connectivity manifold.

Figure 17:
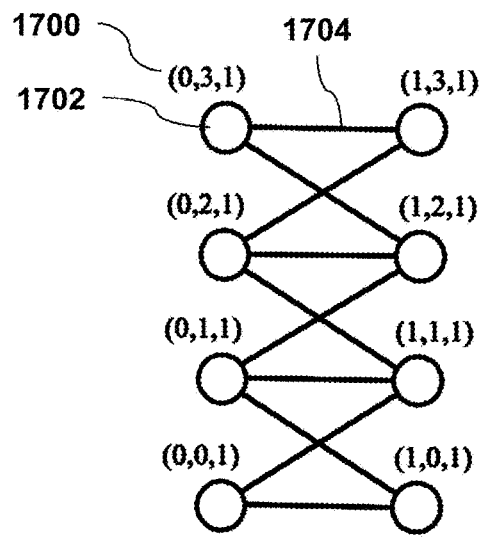
FIG. 17 illustrates node and edge definition in a graph problem, according to an embodiment of the invention. Circles represent nodes, lines connecting these nodes are edges, and the tuples of numbers above each node are the node's unique coordinates (vertex number, collimator index, region bitfield).

The above rule is illustrated in FIG. 17. The triple 1700 represents the coordinates (vertex, collimator index, region bitfield) for node 1702, and 1704 shows an edge connecting two nodes. This figure shows nodes for different collimator angles for vertex 0 and with 4 collimator indexes each (only region bitfield=1 shown). In this hypothetical example, the collimator index can go up/down one index when going between vertex 0 and 1, and so the edges are as shown.

Aspects of the current technology relate to min/max-distance functions that are defined for a path. According to some embodiments, the min/max-distance functions are defined along an edge E as:

$$D^{max}(E)=\Delta\theta(E)\cdot(C_1^{max}\cdot S(b_2)+C_2^{max}/t^{mlc}(E)+C_3^{max}/p^{collimator}(c_2)+C_4^{max}/p^{efficiency}(E))$$

$$D^{min}(E)=\Delta\theta(E)\cdot(C_1^{min}/S(b_2)+C_2^{min}\cdot t^{mlc}(E)+C_3^{min}\cdot p^{collimator}(c_2)+C_4^{min}\cdot p^{efficiency}(E))$$

where the total distance of the path is the sum of the distance of each edge. Here, $\Delta\theta$ is the physical angular distance traveled by the treatment head going from control point 1 to 2. These equations have four terms, each carrying a certain meaning. Each term appears as the inverse of one another in each equation. This reflects the fact that roughly speaking max-distance="goodness" and min-distance=1/"goodness".

According to some embodiments, the definitions and meanings behind each term are:

$$S(b)=(RV_{average}(b)+1)/2\cdot\max(0,A(b)-C_{exposed}A_{exposed}(b))$$

$RV_{average}$ is the average pixel region value of the pixels for the regions defined by bitfield b and entire coefficient has been scaled to be between 0.5 and 1.0, A(b) is the combined area of regions of bitfield b, and the $A_{exposed}(b)$ is the total area exposed by the MLCs at the second control point. This score is higher when moving to control points with large, high score regions, and penalized for having MLCs exposing non-region areas.

$t^{mlc}$ is the time it takes for the MLCs to travel from the configuration specified in control point 1 to control point 2. This term helps the optimization find collimator angles that avoid large jumps in MLC positions.

$p^{collimator}=\sin^2(\theta_{collimator}-\theta_{motion})$. This is a penalty factor that encourages the collimator angle to align with the direction of physical motion of the treatment head.

$p^{efficiency}=(1-\in_{relative})$ where $\in_{relative}=\Delta\theta(E)/\Delta\theta_{max}$. This factor penalizes edges where the beam is almost stationary, so treatment time is not wasted in such locations.

According to some embodiments, using the min-distance function defined above, a shortest path through the graph between any two nodes can be found using a path optimization algorithm, such as that of Dijkstra or with a modification which we describe in the next section dealing with the starting and end points.

Boundary Nodes

According to some embodiments, boundaries of the BEV region connectivity manifold are selected to be the starting and ending nodes of treatment trajectories.

To define boundary nodes, it is necessary to first define boundary vertices in the delivery coordinate space for 1D and 2D spaces (note that the generalization of this to higher dimensions is trivial). A 1D space is made of only vertices and edges, and boundary vertices are those that only touch at most a single edge. Similarly, in a 2D space of vertices, edges and faces, boundary vertices are those that belong to an edge which only touches a single face.

According to some embodiments, a boundary region is defined as follows. Given a region $r=(n_{vertex}, n_{subindex})$, this is a boundary region if one of two conditions applies:

The base vertex is a boundary vertex

Consider the base vertex. If there exists an edge in the delivery coordinate space touching this vertex such that there is no region connection along this edge, then the region is a boundary vertex.

Figure 18:
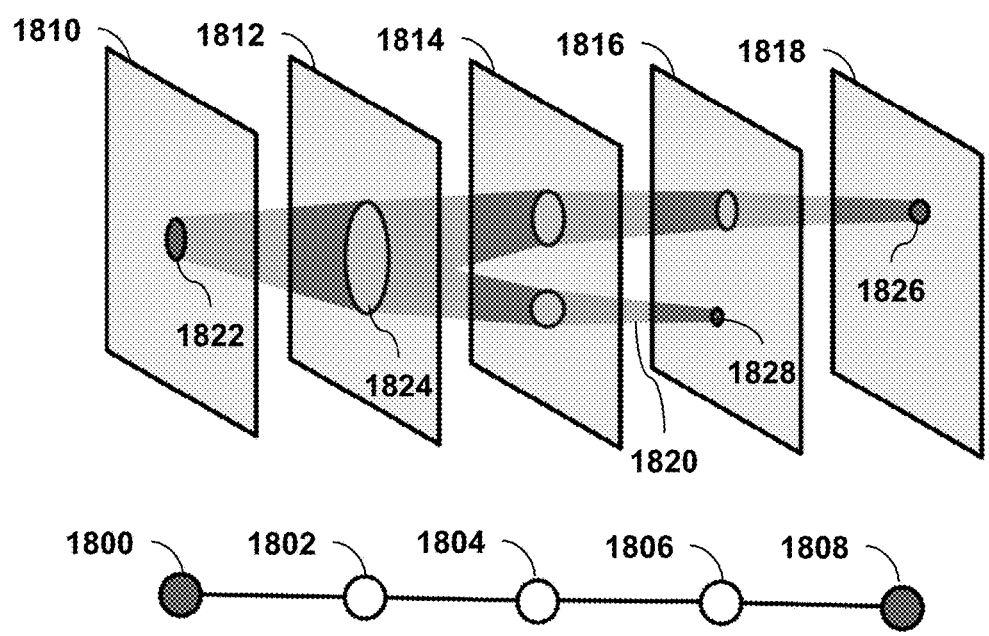
FIG. 18 illustrates boundary node definition, according to an embodiment of the invention. Bottom circles and edges represent the underlying delivery coordinate space, and the BEV planes above each circle are the individual BEV from each vertex. The ovals in each BEV are regions to treat, with shaded connections between each BEV. Dark ovals are boundary nodes.

The latter more complicated condition is illustrated in FIG. 18. The bottom 5 vertices 1800, 1802, 1804, 1806, 1808 represent the delivery coordinate space, with the shaded circles 1800, 1808 being boundary vertices. The 5 planes 1810, 1812, 1814, 1816, 1818 represent the BEV at each of the 5 corresponding vertices, with the ellipses 1822, 1824, 1826, 1828 being identified regions, and the interplane shading 1820 shows which regions are connected. Darker regions 1822, 1826, 1828 are boundary regions. Notice that the regions on the far left 1822 and far right 1826 pass the first condition, and so are trivially identified as boundary. However, the bottom region 1828 at the $4^{th}$ vertex 1806 passes the second condition: all the lightly shaded regions have connections both to the left and right, but the $4^{th}$ vertex bottom region only has a connection to the left.

According to some embodiments, a boundary node is a one such that all the regions denoted by its region bitfield are boundary regions. These boundary nodes form all potential starting and end nodes for the path optimization. Note that if the BEV region connectivity manifold has multiple connected components, then consequentially the search graph also must have multiple connected components of nodes. In this case, the path optimization algorithm can be applied to each connected component separately.

Path Optimization

According to some embodiments, path optimization is performed using a modified form of any traditional path optimization algorithm, with metric given by the min-distance, such as using the algorithm by Dijkstra as the base algorithm with either of the following modifications:

1. Using a family of starting active nodes where the starting active nodes are fixed by a vertex $v_s$ and region bitfield $b_s$; and starting nodes are of the form $(v_s, c, b)$ where c is any collimator index (if cyclic, then all indexes in the first cycle from 0 to max−1), and the region bitfield b satisfies $b \wedge b_s = b$ (the wedge product represents bitwise AND—this equation means that any subset of the regions denoted by $b_s$ are possible).

Figure 19:
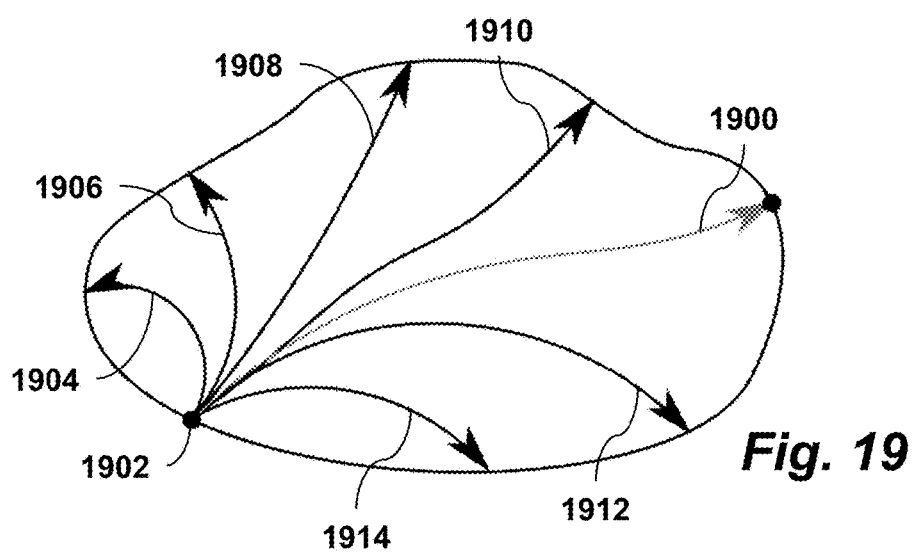
FIG. 19 illustrates a 1-to-N graph search strategy, according to an embodiment of the invention. Starting from a single boundary node, shortest paths to every boundary node are calculated, and the path with the largest max-distance (lighter trajectory) is selected as the best trajectory.

2. Considering all boundary nodes simultaneously as end nodes. Applying the path optimization algorithm until there are no more active nodes, then the algorithm naturally will hit every boundary node. This means that with no increase in algorithmic complexity the search can be modified from a 1-to-1 node search to a 1-to-N node search. The path resulting in the largest max-distance is selected out of the set of paths that run from the starting node to each boundary node. An example is shown in FIG. 19, where the lighter shaded path 1900 is selected as having the largest max-distance out of all the possible paths 1904, 1906, 1908, 1910, 1912, 1914 shown from a given starting node 1902.

According to some embodiments, the 1-to-N search is implemented as follows. A "best boundary node" dictionary that maps vertices to nodes is stored. Whenever the algorithm encounters a boundary node, it consults this dictionary. If the node's vertex is not in the dictionary (not yet visited), it maps that vertex to this node. Otherwise it checks against the existing node in the dictionary and overwrites it only if the current node has larger max-distance. Once all active nodes are exhausted, the node from this dictionary with the largest max-distance is selected and its corresponding path is the one with largest max-distance.

According to some embodiments, the algorithm does not require an end point, but it does require a starting point. An optimal starting point is one that is on as "extremal" a boundary point as possible, such that it has a long path to travel.

According to some embodiments, extremal nodes for each connected component are selected by running the path optimization algorithm once. These extremal nodes are then used as the starting point for the algorithm once more, giving the final trajectory.

According to some embodiments, initial starting nodes can be found by finding the Perron-Frobenius eigenvector for the Markov chain transition matrix given by max-distance values along each edge in the BEV region connectivity manifold in each connected component. Each component of this eigenvector corresponds to a single region, and the "score" of a starting vertex can be defined to be the sum of the score for each region. The vertex with largest such score can be chosen as the starting node.

Figure 20:
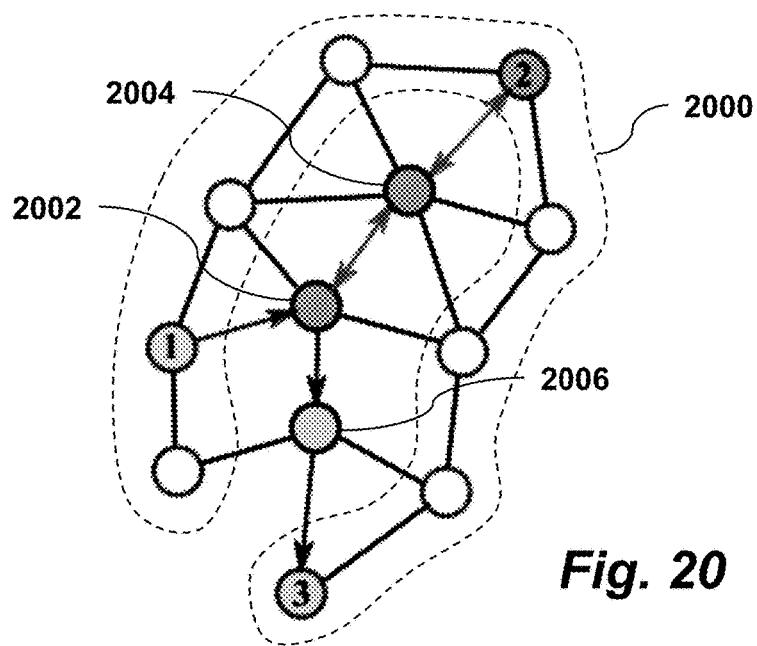
FIG. 20 illustrates a two step optimization process. Starting from an arbitrary node 1 and optimizing gives end point 2. Using 2 as the new start point and optimizing gives end point 3 and in this case the true globally maximal trajectory.

The above approach is demonstrated FIG. 20. Node 1 is the randomly selected starting node, boundary nodes are outlined 2000. The path selected with the largest max-distance from node 1 ends on node 2 and has the resulting illustrated path through nodes 2002, 2004. Re-running the algorithm starting from node 2 then gives ending node 3 and the illustrated path through nodes 2004, 2002, 2006. In this simplified case, it can be seen to have successfully found the path with the largest max-distance, from node 2 to node 3.

According to some embodiments, the selection of extremal starting nodes can be sped up in this first iteration by using simplified distance functions in the path optimization. The previously described distance functions require calculation of the MLC positions of many leaves, which requires significant computation. According to some embodiments, the following distance functions that only use the score term are used in the first pass of the algorithm:

$$D^{max}(E=((v_1,c_1b_1),(v_2,c_2,b_2)))=\Delta\theta \cdot S(b_2)$$

$$D^{min}(E=((v_1,c_1b_1),(v_2,c_2,b_2)))=\Delta\theta/S(b_2)$$

Successive Trajectories

This section describes how successive trajectories can be chosen in a way that maximizes angular spread, and minimizes trajectory interference. There are two basic strategies outlined here: score reweighting, and per-voxel angular flux.

Score Reweighting

According to some embodiments, the score term S(b) used in the distance functions is modified for successive trajectories in a way to discourage trajectory interference. Trajectories "interfere" with one-another when they treat the patient from the same direction, or to a lesser extent the exact opposite direction.

According to some embodiments, the value of S(b) is modified based on this score weight by multiplying it by the minimum of all $SW_r$ such that r is a region represented by the bitfield b. This allows certain nodes in the graph optimization to be favored or discouraged based on existing beam trajectories.

According to some embodiments, given a set of existing trajectories $T_1, \ldots, T_N$, the score weights are determined as follows. Initialize the list of $SW_r$ to the multiplicative unit 1.0 for each region. Next, loop through each trajectory. For trajectory $T_j$, calculate the angular distance from the regions hit by this trajectory to each other region. Take this map of angular distances per region, and for region r with angular distance θ modify $SW_r$ by multiplying it by:

$0.7+0.3\theta/25°$ if θ<25°

$0.85+0.15|180°-\theta|/25°$ if $|180°-\theta|<25°$ 1.0 otherwise

In this way, trajectories having regions that are in the same direction are penalized and regions that are exactly opposite are penalized to a lesser extent. The values of the constants here are chosen so that overlapping has 30% penalty, and opposing has 15% penalty.

Binary Angular Flux

According to some embodiments, encouraging trajectory separation (with one or multiple trajectories) is accomplished through the concept of per-voxel binary angular flux. Dose optimizers in general will perform better with more angles from which the beam originates. It can be inferred that a radiation plan that hits every voxel of the PTV from multiple angles is a good candidate plan for achieving high dose fall off, ensuring PTV coverage and dose conformality. To encapsulate this concept the per-voxel binary angular flux is defined to be the number of unique directions the beam hits a given voxel at with some spherical binary (either hit or not hit) binning scheme. This corresponding concept that allows for counts for each bin to be any non-negative integer is called simply per-voxel angular flux.

Figure 21:
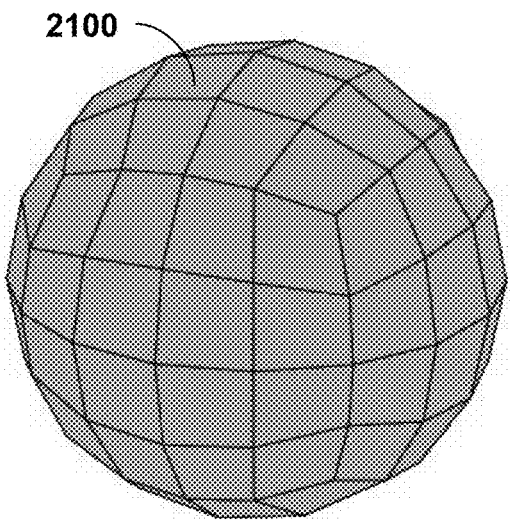
FIG. 21 illustrates a 3D model of 96 face quadrilateralized spherical cube used for binning angular flux, according to an embodiment of the invention.

Aspects of the current technology implement a spherical binning scheme using quadrilateralized spherical cubes, as illustrated in the mesh sphere of FIG. 21. Each face of a cube is divided into 4×4 sub-squares and then each vertex is normalized to have radius 1 to approximate a sphere. This scheme gives ~22 degree side lengths and a total of 6×4×4=96 squares, and the binning scheme is defined to assign to any vector a unique bin. Since each bin is either hit or not, the total per-voxel binary angular flux of a given voxel is represented by a bitfield of 96 bits. Storing one such bitfield for each PTV voxel gives the total PTV binary angular flux.

According to some embodiments, the similar concept of PTV angular flux is defined by letting the bin value be any non-negative number representing the radiation flux.

According to some embodiments, the similar concept of PTV angular flux is defined by letting the bin count be any non-negative integer.

According to some embodiments, the distance function is modified to account for PTV binary angular flux as follows. First, given a set of existing trajectories, compute their contribution to the PTV binary angular flux and use this as the baseline initial binary angular flux state in the optimization. Next, the contribution of each region to a blank PTV binary angular flux state is calculated and stored. In the optimization process, when considering a new node on the graph, the PTV binary angular flux is calculated by bitwise OR-ing the contribution of each region of this node to the PTV binary angular flux, and bitwise OR-ing this with the binary angular flux of the previous node if it exists or the initial binary angular flux if there is no previous node. The new angular flux bin count contributed to the PTV binary angular flux by this candidate node is equal to the total number of bits not in the previous state (i.e., in bitwise notation: candidate & previous).

According to some embodiments, the angular flux bin count is included in the distance function. An example implementation is as follows. To normalize the bin count, the average new angular flux bin count of each region is calculated by comparing against the initial PTV binary angular flux. The normalized angular flux contribution (NAFC) of the candidate node is then given by NAFC(b)= (new angular flux bin count/max(1, average new angular flux bin count)), and the score contribution to the distances functions is modified to be:

$$S(b) = NAFC(b)/2 + (0.5 RV_{average}(b) + 0.5)/2 \cdot max(0, A(b) - C_{exposed} A_{exposed}(b))$$

Topological Considerations

The algorithm described above can only be used to generate trajectories that have a start and end node, which are called open trajectories. According to some embodiments, the technology uses only closed trajectories, essentially "loops". It could be the case, depending on the patient geometry, that the BEV region connectivity manifold has no boundaries, which would preclude the possibility of choosing endpoints. Even if the manifold has boundaries, it could be the case that a closed trajectory would have larger max-distance than any possible open trajectory.

Figure 22A:
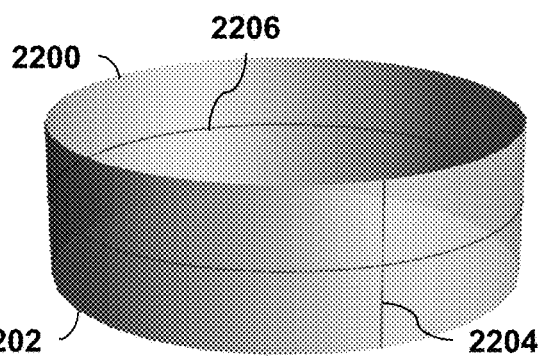
FIGS. 22A-C show examples of delivery coordinate spaces with different topologies, according to an embodiment of the invention.

Shown in FIG. 22A is the example case of a strip. The strip has a boundary along the top 2200 and bottom 2202, so it is possible to generate trajectories like the vertical line 2204. However, there is also the possibility of a trajectory 2206 looping around the entire strip. In this case there are both open and closed trajectories.

Figure 22B:
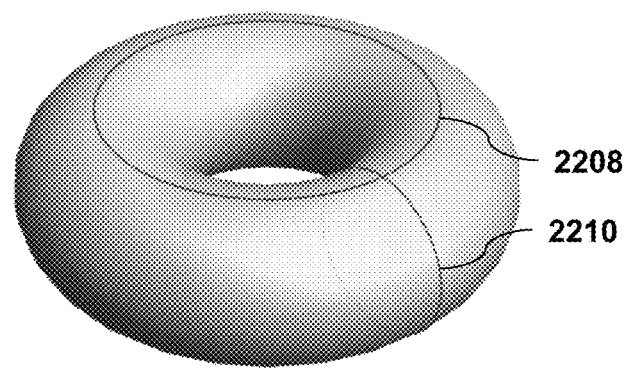

Shown in FIG. 22B is the example case of a torus. A torus has no boundary, so there would only be closed trajectories to optimize on it. Shown are two possible trajectories 2208, 2210 that loop around the torus in two different ways (these are fundamental cycles of the torus). Regardless of how the two trajectories are moved on the surface of the torus, they cannot be deformed into each other, or into an arbitrarily small cycle. Since these cannot be deformed to a point, these are called non-trivial closed trajectories. According to some embodiments, by starting with any representative non-trivial closed trajectory and deforming it to minimize the min-distance function will give an optimized closed trajectory.

Figure 22C:
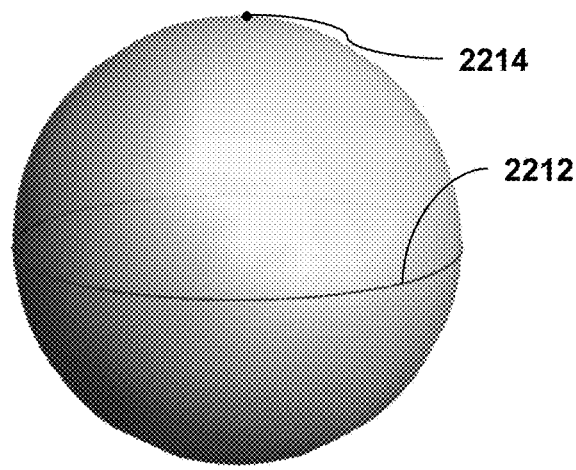

Shown in FIG. 22C is the example case of a sphere. A sphere also has no boundary, but unlike the above case of a torus, it does not have non-trivial closed trajectories. Notice that the circle 2212 drawn on the sphere can be translated upward, and brought to a point at the upper pole 2214. This example demonstrates a trivial closed trajectory. A practical problem with trivial closed trajectories is that since perturbations can bring the curve to an arbitrarily small point, finding the shortest path that can be perturbed from this will always come up with a zero-length solution consisting of a single point. This means that an optimized closed trajectory in this case cannot be found by minimizing a distance function. However, by intuitively looking at the case of the sphere, it can be reasonably presumed that great circles make good candidates for "optimal" trajectories. The identifying property of a great circle is that it is a closed geodesic. For the BEV region connectivity manifold, there always exist approximately geodesic trajectories that are closed.

Homology Computation

This section discusses how homology can be used to determine the existence of non-trivial trajectories in the BEV region connectivity manifold, and how they are constructed. According to some embodiments, the BEV region connectivity manifold is triangulated into a simplicial complex. Simplicial homology theory is used to calculate the first homology group, and how the basis vectors of the first homology group are identified as non-trivial closed trajectories in the BEV region connectivity manifold.

According to some embodiments, for manifold X, the k-th homology group $H_k(X)$ measures the k-dimensional holes. Since trajectories are 1D objects, the embodiment only needs to consider $H_1(X)$. The homology group can be calculated by constructing a simplicial complex C(X) which triangulates the manifold X, and using the theory of simplicial homology. If $C_k$ is used to denote the simplicial k-chain free Abelian group of k-dimensional simplexes of C(X), then the standard boundary operator $\partial_k: C_k \rightarrow C_{k-1}$ can be defined. Two special groups are then defined on these groups, $Z_k$=ker $\partial_k$, and $B_k$=im $\partial_{k+1}$. $Z_k$ is the group of cycles (those which have no boundary), while $B_k$ is the group of boundaries (those which are the boundary of some k+1-chain). Finally, the homology group $H_k(X)$ is defined to be the quotient group of cycles over boundaries, $Z_k/B_k$.

According to some embodiments, the following computational approach is used: First, taking the k-simplexes as the basis vectors, the boundary operators $\partial_k$ are converted to their matrix representation by acting on these k-simplexes. $H_k(X)$ can be calculated by determining the kernel of the matrix $\partial_k$ and the image of the matrix $\partial_{k+1}$.

Let $A_k$ be the matrix representation of $\partial_k$ with dimension $n_{k-1} \times n_k$, where $n_k$ is the rank of $C_k$. To calculate the kernel, column-reduce $A_k$ while applying the same column operations on the identity matrix with side length $n_k$, $I_{n_k}$. Denoting the column reduced identity matrix as $U_k$, then the column reduced version of $A_k$ is given by $A_k U_k$. Letting the rank of $A_k$ be $r_k$, then the number of non-zero columns of $(A_k U_k)$ will be $r_k$. This means that the final $(n_k - r_k)$ columns of $(A_k U_k)$ will be all zeros, and a set of basis vectors for the kernel of $A_k$ is given by the last $(n_k - r_k)$ columns of $U_k$.

Next, applying the same column reduction operations in reverse to the identity matrix $I_{n_k}$ gives the inverse matrix $U_k^{-1}$. The image of $A_{k+1}$ is found by calculating $(U_k^{-1} A_{k+1})$. Letting $\{b_i\}$ be the row numbers of non-zero rows of $(U_k^{-1} A_{k+1})$, then a basis of the image of $A_{k+1}$ is given by the $\{b_i\}$ columns of $U_k$.

If indexing of columns of $U_k$ runs from 1 to $n_k$, then columns $\{z=r_{k+1}, r_{k+2}, \ldots n_k\}$ of $U_k$ form a basis for $Z_k$, and the columns $\{b_i\}$ of $U_k$ form a basis for $B_k$. It will always be the case that $\{b_i\} \subseteq \{z_i\}$ since $B_k \subseteq Z_k$. This means that a basis for $H_k(X)$ is given by the columns in $\{h_i\}=\{z_i\}\backslash\{b_i\}$ of $U_k$. Furthermore, the number of elements of $\{h_i\}$ is the rank of $H_k(X)$, and hence the number of k-dimensional holes. In the case of 1D cycles, sample closed loops (trajectories) are given by these basis elements of $H_1(X)$. This describes the computational method of coming up with non-trivial closed trajectories.

Closed Trajectory Optimization

Figure 23:
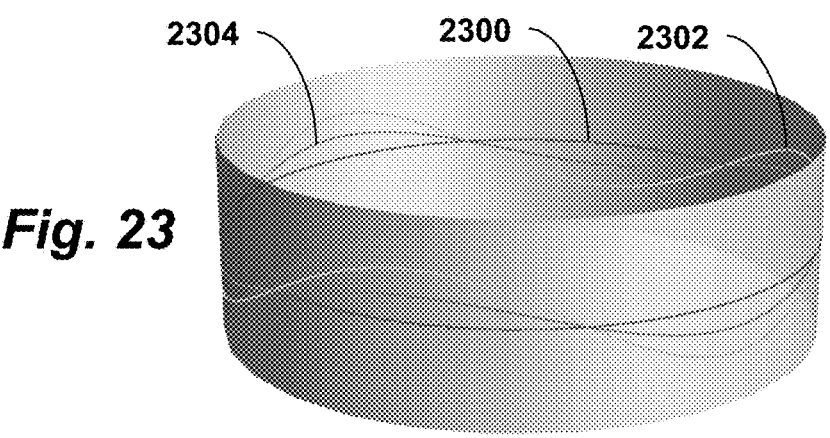
FIG. 23 illustrates an optimal trajectory around a strip (dark line) and two trajectory perturbations around this trajectory (lighter lines), according to an embodiment of the invention.

According to some embodiments, using the calculation of homology group above, example non-trivial closed trajectories are constructed. The optimal homologically equivalent trajectory is defined to be the one that minimizes the min-distance function amongst all possible trajectories that can be reached through perturbation. Shown in FIG. 23 are three such trajectories 2300, 2302, 2304 that are perturbations of each other. The lighter paths 2302, 2304 have longer lengths, with the dark straight line 2300 being the one with minimal distance (optimal trajectory).

For trivial closed trajectories, closed geodesics cannot be found by minimizing the distance of a trajectory through perturbation. According to some embodiments, an estimate for such a geodesic is found through the following algorithm: First, pick some point with a "high" score (for instance using the above explained Markov chain and Perron-Frobenius eigenvector). Next, run the open trajectory optimization algorithm explained above starting at this point. Instead of keeping track of boundary nodes, keep track of the node with the largest max-distance out of all nodes. Note that this node will be, by nature of the max-distance function, "furthest" from the starting point. Treating this node as the only "boundary" point, the algorithm produces all optimized trajectories with the given starting node and final node (including all possible starting and stopping collimator angles and region selections). The final trajectory is then found by picking two of these trajectories that meet at these starting and final nodes in a smooth way, forming a closed trajectory.

Trajectory Polishing

This section explains how to incrementally improve the quality of trajectories before passing them to a final MLC modulation optimizer engine.

Trajectory Smoothing

Due to the discretization of the delivery coordinate space, the resulting trajectories can have sharp edges which result in excessive jerking in the physical motion of the delivery device. In the top figure here is shown an actual optimized trajectory in ($\theta_{gantry}$, $\theta_{couch}$) space. The original regular rectangular grid of the delivery coordinate space causes the trajectory to consist of 90 degree turns where the gantry suddenly stops and the couch suddenly starts, and vice versa. This motion can cause stress on the delivery device, and can be uncomfortable for the patient.

Figure 24A:
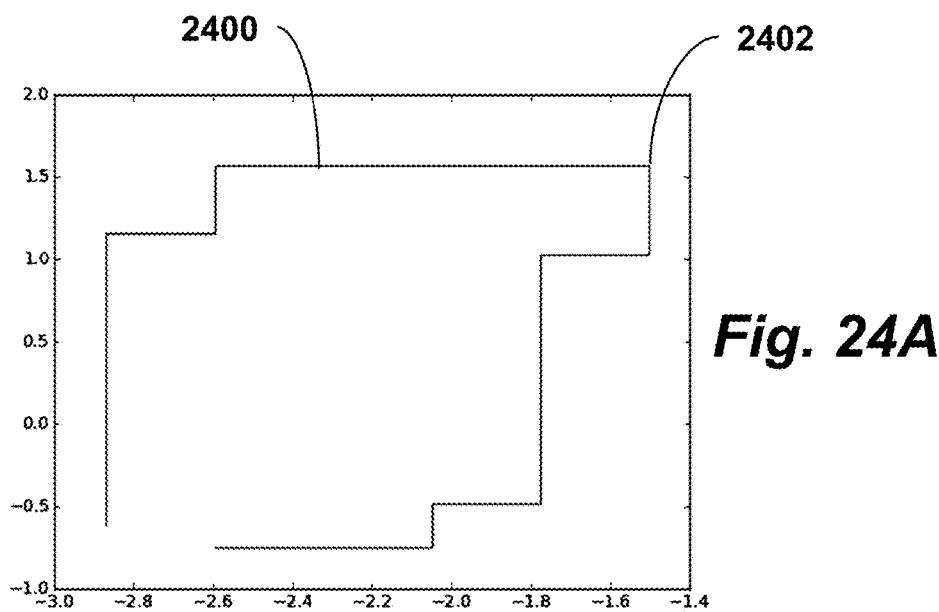
FIGS. 24A-B illustrate the use of B-spline for smoothing trajectories that have kinks, according to an embodiment of the invention.
Figure 24B:
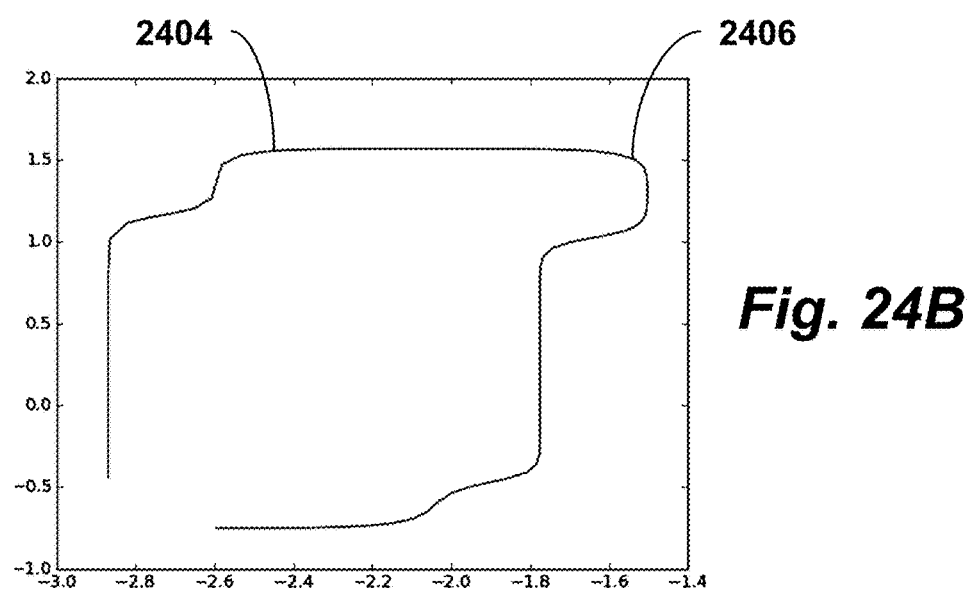

According to some embodiments, to smooth the trajectory, a standard B-spline is fit to the directional delivery coordinate points (rotational coordinate can be included too if desired). This curve is then parameterized by physical angular displacement of the treatment head, and the curve is discretized once again so that each point is of equal angular distance apart using linear interpolation with angular displacement as the independent variable. The result of applying this algorithm with double the number of control points is illustrated in FIGS. 24A and 24B. The horizontal axes represents gantry angle and the vertical axes couch angle. Path 2400 has a kink at 2402, but this is smoothed out in path 2404 (B-spline of 2400) and has smooth corner at 2406.

Field Splitting

Aspects of the current technology may lead to BEV regions to expose that contain holes. In such a case it is impossible to block the region internal holes using the proposed MLCs while leaving the surrounding region unaffected. According to some embodiments, if a trajectory has regions with holes that significantly handicap performance, then the trajectory can be improved by attempting to split the field into two or more trajectories using a pair of collimating jaws.

Figure 25:
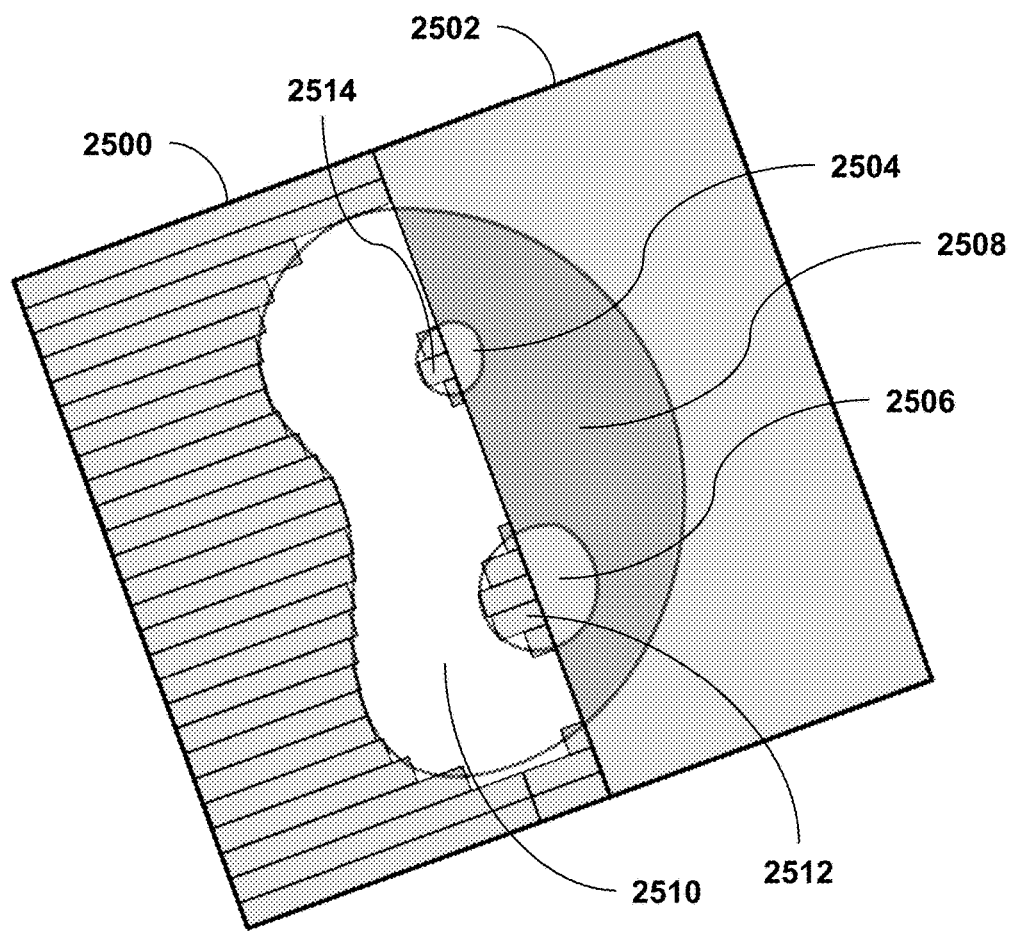
FIG. 25 illustrates the use of jaw splitting to treat regions that have holes while still shielding the holes from radiation exposure, according to an embodiment of the invention.

An example is illustrated in FIG. 25. The background region has two holes 2504, 2506 that should be shielded if possible. If the field is split into two halves 2500, 2502 as shown, then it becomes possible for the MLCs 2512 and 2514 to completely shield the interior holes. In this figure the right half is blocked off with the jaw and so good region 2508 is blocked and only good region 2510 is being treated.

According to some embodiments, when performing a graph optimization on this split trajectory, since the angle of the jaws and MLCs are locked together, only one additional degree of freedom is introduced: x jaw position. In the above figure this x jaw position is such that the split line runs approximately down the middle of the two holes. With the inclusion of a field split, since the interior holes can potentially be blocked by the MLC, the score of this trajectory will be higher.

Selecting Trajectories for a Radiotherapy Plan

The above discussions describe how to construct and polish a single trajectory. However, to build a satisfactory radiation therapy plan it might be necessary to combine multiple trajectories into a single plan. According to some embodiments, successive trajectories should are chosen by considering existing trajectories and ensuring that the new trajectories are complementary, for instance to help ensure coverage of the PTV or preemptively discourage formation of hotspots.

Angular Flux Modification to BEV Region Connectivity Manifold

According to aspects of the technology, the concept of coverage is partially addressed by using the PTV binary angular flux in the distance function. The weakness of this is that the possible contributions to the PTV binary angular flux is restricted by the choice of regions making up the BEV region connectivity manifold (if a certain PTV voxel is not hit by any region, there is no way for the graph optimization to reach it). According to some embodiments, the BEV region connectivity manifold used for successive trajectories can be a function of the set of existing trajectories, with regions expanded/contracted to improve coverage/reduce hotspots.

According to some embodiments, this is accomplished by using the PTV (binary) angular flux concept. Voxels lacking coverage are detected by looking for voxels with low binary angular flux counts, while voxels being overcovered are detected by looking for voxels with high (non-binary) angular flux counts (can consider both high counts to individual angular bins or high counts to bins overall).

According to some embodiments, once a set of PTV voxels to cover/block is determined, the regions are modified in the following way. For each beamlet in each BEV, the contribution to the set of under-covered voxels is calculated. This is a count of how many novel angles each of these voxels is hit by the given beamlet given the PTV binary angular flux contributed by the existing trajectories. This count acts as a coverage score for each beamlet. Similarly, the contribution of each beamlet for each BEV to the set of overhit voxels is determined by counting the number of such voxels hit by the beamlet that contribute negatively to being overhit (if a voxel is overhit due to high overall bin count, any angle contributes negatively, whereas a voxel being overhit due to a high individual bin count only contributes negatively for beamlets that add to this angular bin). This count acts as a overhit score for each beamlet.

According to some embodiments, the overall beamlet angular score of each beamlet is then the coverage score minus the overhit score. By then shifting the region value in the most recent BEV region connectivity manifold of each beamlet by an amount proportional to its beamlet angular score, then linearly rescaling all region values such that approximately the same number of beamlets fall in the 0.0 to 1.0 range, these new region values define a new BEV region connectivity manifold.

Dose-Based Coverage Boosting and Leakage Blocking

According to some embodiments, a strategic expansion/contraction of the MLCs is used to increase coverage/block hotspots. A set of points where the dose is too low or too high is first identified by selecting a set of dose points to investigate and performing a radiation dose calculation to determine the dose on a set of points in the patient. When checking for coverage, the points can be selected as follows: Start with the vertices which make up the PTV polygon meshes, and set the dose points to be equal to these vertices moved inward by a fixed amount (Ex. 5 mm), where inward is defined by the mesh's surface normal vectors. These dose points probe the dose within this depth in the PTV. The maximum dose to these points is called the reference dose, $D_{ref}$. According to some embodiments, the coverage boosting points are then chosen to be the points whose total dose is less than 10% of $D_{ref}$. Similarly, to check for and correct dose leakage, dose points can be selected by moving the PTV vertices a fixed amount outward, and choosing leakage blocking points as those points whose dose is greater than 50% of $D_{ref}$. Another choice of dose points for checking leakage that can be used are for instance the vertices that make up the OAR polygon meshes.

Figure 26:
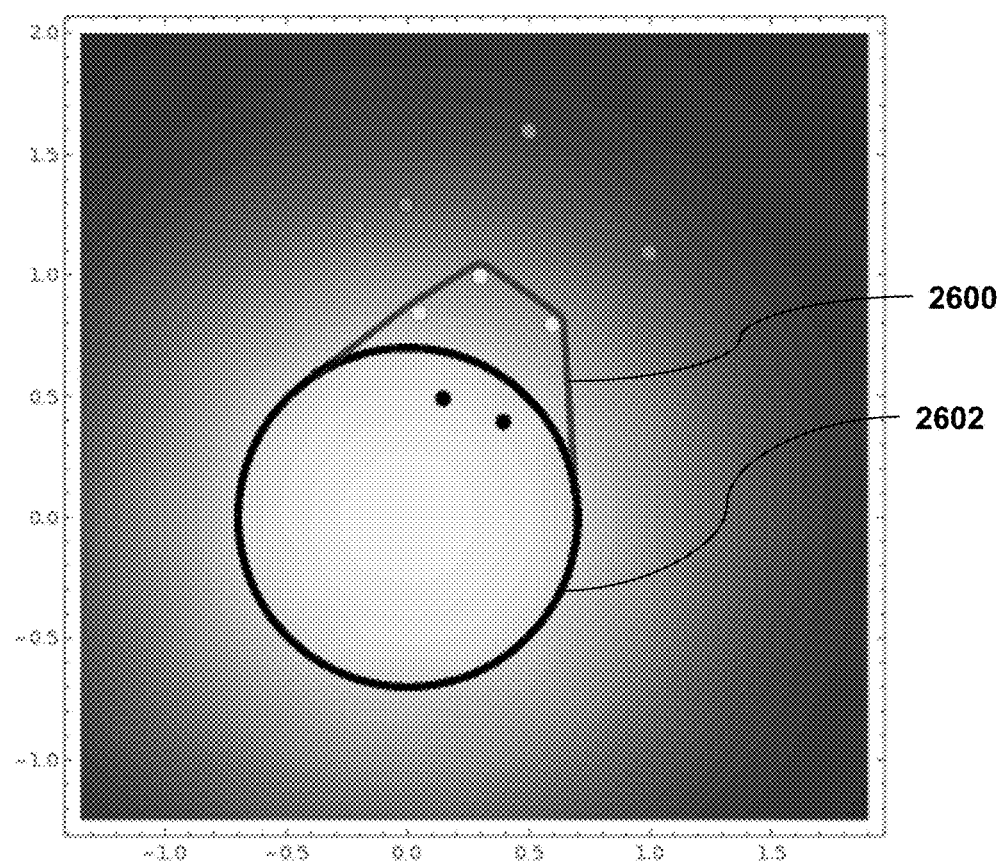
FIG. 26 illustrates a technique of expanding regions to encompass PTV points that are undercovered, according to an embodiment of the invention.

An example illustration of the algorithm in the case of 9 coverage boosting points is shown in FIG. 26. Nine points are drawn on a 2D BEV from an arbitrary treatment head direction on a trajectory. The background shading indicates the score, and the circle outlines the single proposed region to expose for this BEV. Conceptually, the algorithm seeks to increase the size of the region to include all these coverage-boosting points. However, the excluded points are very far away, and the included points are already within the region. The identified points seem to be good candidates, as they are close to the original region to expose.

According to some embodiments, to decide which points to select when expanding the region, a $\Delta S_{threshold}$ score threshold buffer value is first fixed, and if the score at a coverage boosting point satisfies $S > S_{threshold} - \Delta S_{threshold}$, then this point is accepted and the region size is increased to accommodate it. This can be accomplished by using alpha shapes to increase the size of the regions, as illustrated by the line 2600 extending off of the large circle 2602 in FIG. 26, but instead it is optimal to simply choose to open up the MLCs sufficiently to expose these additional points.

According to some embodiments, a coverage-boosting algorithm applied to a set of coverage boosting points is applied as follows:
Iterate through each control point in the trajectory.
Transform the coverage boosting points into the beam frame at the current control point.
Determine the score of each coverage boosting point by using its (x,y) coordinates in this beam frame, and accept it if the score obeys $S > S_{threshold} - \Delta S_{threshold}$.
For each accepted coverage boosting point, determine the minimum MLC leaf coordinate change required to the to expose a 2 mm circle around this point, and accept this change only if the total change of a leafs coordinate is less than 5 cm

REFERENCES

[1] K. Otto, "Volumetric modulated arc therapy: IMRT in a single gantry arc," Med Phys, vol. 35, no. 1, pp. 310-317, 2008.
[2] C. X. Yu, "Intensity-modulated arc therapy with dynamic multileaf collimation: an alternative to tomotherapy," Phys Med Biol, vol. 40, no. 9, pp. 1435-1449, September 1995.
[3] P. Zhang, L. Happersett, Y. Yang, Y. Yamada, G. Mageras, and M. Hunt, "Optimization of Collimator Trajectory in Volumetric Modulated Arc Therapy: Development and Evaluation for Paraspinal SBRT," Radiation Oncology Biology, vol. 77, no. 2, pp. 591-599, June 2010.
[4] Y. Yang, P. Zhang, L. Happersett, J. Xiong, J. Yang, M. Chan, K. Beal, G. Mageras, and M. Hunt, "Choreographing couch and collimator in volumetric modulated arc therapy," Radiation Oncology Biology, vol. 80, no. 4, pp. 1238-1247, July 2011.
[5] E. B. Podgorsak, A. Olivier, M. Pla, P. Y. Lefebvre, and J. Hazel, "Dynamic stereotactic radiosurgery," Radiation Oncology Biology, vol. 14, no. 1, pp. 115-126, January 1988.
[6] A. Pugachev and L. Xing, "Incorporating prior knowledge into beam orientation optimization in IMRT," Radiation Oncology Biology, vol. 54, no. 5, pp. 1565-1574, December 2002.
[7] A. Pugachev and L. Xing, "Computer-assisted selection of coplanar beam orientations in intensity-modulated radiation therapy," Phys Med Biol, vol. 46, no. 9, pp. 2467-2476, September 2001.

[8] Y. Ma, R. Popple, T.-S. Suh, and L. Xing, "Beam•s-Eye-View Dosimetrics-Guided Inverse Planning for Aperture-Modulated Arc Therapy," Radiation Oncology Biology, vol. 75, no. 5, pp. 1587-1595, December 2009.

[9] L. B. Marks, E. D. Yorke, A. Jackson, R. Ten Haken, L. S. Constine, A. Eisbruch, S. M. Bentzen, and J. O. Deasy, "Use Of Normal Tissue Complication Probability Models In The Clinic," Radiation Oncology Biology, vol. 76, no. S, pp. S10-S19, March 2010.

[10] B. Fahimian, V. Yu, K. Horst, L. Xing, and D. Hristov, "Trajectory modulated prone breast irradiation: A LINAC-based technique combining intensity modulated delivery and motion of the couch," Radiother Oncol, vol. 109, no. 3, pp. 475-481, December 2013.

[11] B. Fahimian, L. Xing, S. Geneser, and D. Hristov, "Dynamic multi-axes trajectory optimization and delivery method for radiation treatment." Patent US 20130142310 A1

[12] H. Kim, R. Li, R. Lee, and L. Xing, "Beam's-eye-view dosimetrics (BEVD) guided rotational station parameter optimized radiation therapy (SPORT) planning based on reweighted total-variation minimization," Phys Med Biol, pp. 71-82, February 2015.

[13] J. Liang, T. Atwood, R. von Eyben, B. Fahimian, E. Chin, K. Horst, K. Otto, and D. Hristov, "Trajectory Modulated Arc Therapy: A Fully Dynamic Delivery With Synchronized Couch and Gantry Motion Significantly Improves Dosimetric Indices Correlated With Poor Cosmesisin Accelerated Partial Breast Irradiation," Radiation Oncology Biology, vol. 92, no. 5, pp. 1148-1156, August 2015.

[14] P. Dong, P. Lee, D. Ruan, T. Long, E. Romeijn, Y. Yang, D. Low, P. Kupelian, and K. Sheng, "4pi Non-Coplanar Liver SBRT: A Novel Delivery Technique," Radiation Oncology Biology, vol. 85, no. 5, pp. 1360-1366, April 2013.

[15] P. Dong, P. Lee, D. Ruan, T. Long, E. Romeijn, D. A. Low, P. Kupelian, J. Abraham, Y. Yang, and K. Sheng, "Noncoplanar Stereotactic Body Radiation Therapy for Centrally Located or Larger Lung Tumors," Radiation Oncology Biology, vol. 86, no. 3, pp. 407-413, July 2013.

[16] G. Smyth, J. C. Bamber, P. M. Evans, and J. L. Bedford, "Trajectory optimization for dynamic couch rotation during volumetric modulated arc radiotherapy," Phys Med Biol, vol. 58, no. 22, pp. 8163-8177, November 2013.

[17] R. L. MacDonald and C. G. Thomas, "Dynamic trajectory-based couch motion for improvement of radiation therapy trajectories in cranial SRT," Med Phys, vol. 42, no. 5, pp. 2317-2325, May 2015.

[18] R. L. MacDonald and C. G. Thomas, "Procédé et système pour le traitement du cancer avec un rayonnement." Patent WO2016008052 A1

[19] D. Papp and J. Unkelbach, "Direct leaf trajectory optimization for volumetric modulated arc therapy planning with sliding window delivery," Med Phys, vol. 41, no. 1, p. 011701, 2014.

[20] D. Papp, T. Bortfeld, and J. Unkelbach, "A modular approach to intensity-modulated arc therapy optimization with noncoplanar trajectories," Phys Med Biol, pp. 5179-5198, June 2015.

[21] E. Wild, M. Bangert, S. Nill, and U. Oelfke, "Noncoplanar VMAT for nasopharyngeal tumors: Plan quality versus treatment time," Med Phys, vol. 42, no. 5, pp. 2157-2168, May 2015.

The invention claimed is:

1. A method for radiation therapy treatment using a radiation delivery device, the method comprising:
providing a patient model, dosimetric constraints, delivery motion constraints, and delivery coordinate space of the radiation delivery device, wherein the delivery coordinate space is represented as a mesh with vertices connected by edges, where the vertices correspond to directions of a beam eye view (BEV) of the radiation delivery device, where each BEV has corresponding area elements resulting from beam collimation;
constructing BEV region connectivity manifolds from the patient model, the dosimetric constraints, the delivery coordinate space, and existing beam trajectories, wherein each of the BEV region connectivity manifolds represents connections between contiguous 2D target regions, wherein each of the 2D target regions is defined at each of the vertices of the delivery coordinate space;
selecting beam trajectories based on region connectedness information in the BEV region connectivity manifolds, the dosimetric constraints, the delivery motion constraints, and the existing beam trajectories; and
delivering radiation using the radiation delivery device in accordance with the selected beam trajectories.

2. The method of claim 1 wherein
selecting beam trajectories is also based on a BEV dose section and a BEV score section, wherein the term "section" refers to a section of a BEV fiber bundle.

3. The method of claim 1 wherein
selecting beam trajectories uses a max-distance function to select among trajectories found using a min-distance function.

4. The method of claim 3 wherein
selecting beam trajectories maximizes angular spread and minimizes trajectory interference by including in the min-distance function and max-distance function a per-voxel angular flux defined to be the number of unique directions at which the beam hits a given voxel with some spherical binning scheme.

5. The method of claim 1 wherein
constructing the BEV region connectivity manifold comprises:
i) at each vertex, identifying contiguous 2D target regions using a binary selection criterion to identify apertures for treatment;
ii) identifying connections between contiguous 2D target regions of neighboring vertices.

6. The method of claim 5 wherein
constructing the BEV region connectivity manifold comprises:
expanding regions whose voxels have low binary angular flux counts; and
contracting regions whose voxels have high (non-binary) angular flux counts;
wherein the angular flux counts are defined to be the number of unique directions at which the beam hits a given voxel with some spherical binning scheme.

7. The method of claim 5
wherein the binary selection criterion is based on a BEV dose section, a BEV score section, and existing beam trajectories.

8. The method of claim 1 further comprising
generating a BEV dose section representing BEV dosimetrics for each area element of the BEV at each vertex in the delivery coordinate space; and generating a BEV score section representing a measure of goodness for treatment at each area element of each vertex in delivery coordinate space.

* * * * *